(12) United States Patent
Eltoukhy et al.

(10) Patent No.: US 12,048,928 B2
(45) Date of Patent: Jul. 30, 2024

(54) MICRODEVICES AND BIOSENSOR CARTRIDGES FOR BIOLOGICAL OR CHEMICAL ANALYSIS AND SYSTEMS AND METHODS FOR THE SAME

(71) Applicant: Illumina, Inc., San Diego, CA (US)

(72) Inventors: Helmy A. Eltoukhy, San Diego, CA (US); Tarun Khurana, San Diego, CA (US); Behnam Javanmardi, San Diego, CA (US); Poorya Sabounchi, San Diego, CA (US); Majid Aghababazadeh, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 17/848,840

(22) Filed: Jun. 24, 2022

(65) Prior Publication Data
US 2022/0323956 A1    Oct. 13, 2022

Related U.S. Application Data

(60) Continuation of application No. 16/529,397, filed on Aug. 1, 2019, now Pat. No. 11,400,446, which is a
(Continued)

(51) Int. Cl.
*B01L 3/00* (2006.01)
*B01L 7/00* (2006.01)
(Continued)

(52) U.S. Cl.
CPC ....... *B01L 3/502715* (2013.01); *B01L 3/5085* (2013.01); *B01L 7/52* (2013.01);
(Continued)

(58) Field of Classification Search
CPC ........ B01L 3/502715; B01L 2200/028; B01L 2200/027; B01L 2200/026;
(Continued)

(56) References Cited

U.S. PATENT DOCUMENTS

| 5,141,651 A | 8/1992 | Giddings |
| 5,304,487 A | 4/1994 | Wilding et al. |

(Continued)

FOREIGN PATENT DOCUMENTS

| EP | 1542010 | 6/2005 |
| EP | 1669754 | 6/2006 |

(Continued)

OTHER PUBLICATIONS

International Search Report and Written Opinion in PCT/US2011/057111 issued Mar. 26, 2012.

*Primary Examiner* — Brian J. Sines
(74) *Attorney, Agent, or Firm* — Illumina, Inc.

(57) ABSTRACT

A flow cell including inlet and outlet ports in fluid communication with each other through a flow channel that extends therebetween. The flow channel includes a diffuser region and a field region that is located downstream from the diffuser region. The field region of the flow channel directs fluid along reaction sites where desired reactions occur. The fluid flows through the diffuser region in a first flow direction and through the field region in a second flow direction. The first and second flow directions being substantially perpendicular.

8 Claims, 22 Drawing Sheets

Related U.S. Application Data continuation of application No. 15/936,165, filed on Mar. 26, 2018, now Pat. No. 10,406,519, which is a division of application No. 15/205,275, filed on Jul. 8, 2016, now Pat. No. 9,937,497, which is a continuation of application No. 14/729,809, filed on Jun. 3, 2015, now Pat. No. 9,387,476, which is a continuation-in-part of application No. 13/882,088, filed as application No. PCT/US2011/057111 on Oct. 20, 2011, now Pat. No. 9,096,899.

(60) Provisional application No. 61/407,350, filed on Oct. 27, 2010.

(51) Int. Cl.
*C12Q 1/6869* (2018.01)
*C12Q 1/6874* (2018.01)

(52) U.S. Cl.
CPC ......... *C12Q 1/6869* (2013.01); *C12Q 1/6874* (2013.01); *B01L 2200/025* (2013.01); *B01L 2200/04* (2013.01); *B01L 2200/082* (2013.01); *B01L 2200/10* (2013.01); *B01L 2200/16* (2013.01); *B01L 2300/022* (2013.01); *B01L 2300/023* (2013.01); *B01L 2300/048* (2013.01); *B01L 2300/0627* (2013.01); *B01L 2300/0636* (2013.01); *B01L 2300/0645* (2013.01); *B01L 2300/0654* (2013.01); *B01L 2300/0819* (2013.01); *B01L 2300/0877* (2013.01); *B01L 2300/161* (2013.01); *B01L 2300/165* (2013.01); *B01L 2400/0457* (2013.01); *B01L 2400/0487* (2013.01); *B01L 2400/0622* (2013.01)

(58) Field of Classification Search
CPC .... B01L 2200/025; B01L 7/52; B01L 3/5085; B01L 3/00; B01L 2400/0622; B01L 2400/0487; B01L 2400/0457; B01L 2300/165; B01L 2300/0877; B01L 2300/0819; B01L 2300/0654; B01L 2300/0645; B01L 2300/0636; B01L 2300/0627; B01L 2300/048; B01L 2300/023; B01L 2300/022; B01L 2200/16; B01L 2300/10; B01L 2200/082; B01L 2200/04; C12Q 1/6869; C12Q 1/6874; G01N 21/00
See application file for complete search history.

(56) References Cited

U.S. PATENT DOCUMENTS

| | | |
|---|---|---|
| 5,427,663 A | 6/1995 | Austin et al. |
| 5,843,767 A | 12/1998 | Beattie |
| 5,971,158 A | 10/1999 | Yager et al. |
| 6,033,544 A | 3/2000 | Demers et al. |
| 6,488,896 B2 | 12/2002 | Weigl et al. |
| 6,548,263 B1 | 4/2003 | Kapur et al. |
| 7,419,638 B2 | 9/2008 | Saltsman et al. |
| 7,595,883 B1 | 9/2009 | El Gamal et al. |
| 7,718,130 B1 | 5/2010 | Shinar et al. |
| 8,023,113 B2 | 9/2011 | El Gamal et al. |
| 8,236,532 B2 | 8/2012 | Ronaghi et al. |
| 8,313,904 B2 | 11/2012 | El Gamal |
| 8,361,716 B2 | 1/2013 | Patil |
| 2001/0055817 A1 | 12/2001 | Malmqvist et al. |
| 2003/0111494 A1 | 6/2003 | Lin et al. |
| 2003/0118716 A1 | 6/2003 | Bass et al. |
| 2005/0106066 A1 | 5/2005 | Saltsman et al. |
| 2005/0130173 A1 | 6/2005 | Leamon et al. |
| 2005/0214863 A1 | 9/2005 | McDevitt et al. |
| 2006/0160231 A1 | 7/2006 | Nadel et al. |
| 2006/0227325 A1 | 10/2006 | Rulison et al. |
| 2006/0228256 A1 | 10/2006 | McDevitt et al. |
| 2007/0086918 A1 | 4/2007 | Hartley et al. |
| 2007/0098600 A1 | 5/2007 | Kayyem |
| 2009/0026082 A1 | 1/2009 | Rothberg et al. |
| 2009/0052563 A1 | 2/2009 | Kim et al. |
| 2009/0075838 A1 | 3/2009 | El Gamal et al. |
| 2009/0019732 A1 | 8/2009 | El Gamal et al. |
| 2009/0203086 A1 | 8/2009 | Chen et al. |
| 2009/0286299 A1 | 11/2009 | Ronaghi et al. |
| 2010/0173303 A1 | 7/2010 | Ronaghi et al. |
| 2011/0134420 A1 | 6/2011 | Matsumoto et al. |
| 2012/0052563 A1 | 3/2012 | Liang et al. |
| 2012/0143531 A1* | 6/2012 | Davey ............ G01N 33/48785 73/40.5 R |
| 2012/0295262 A1 | 11/2012 | Ronaghi et al. |
| 2013/0040863 A1 | 2/2013 | Straus et al. |
| 2013/0078623 A1 | 3/2013 | El Gamal et al. |
| 2013/0079232 A1 | 3/2013 | Kain et al. |
| 2013/0274136 A1 | 10/2013 | Mcdevitt et al. |

FOREIGN PATENT DOCUMENTS

| | | |
|---|---|---|
| EP | 1762300 | 3/2007 |
| EP | 2352035 | 1/2010 |
| WO | 2003/087410 | 10/2003 |
| WO | 2006/136990 | 12/2006 |
| WO | 2009/111696 | 9/2009 |

* cited by examiner

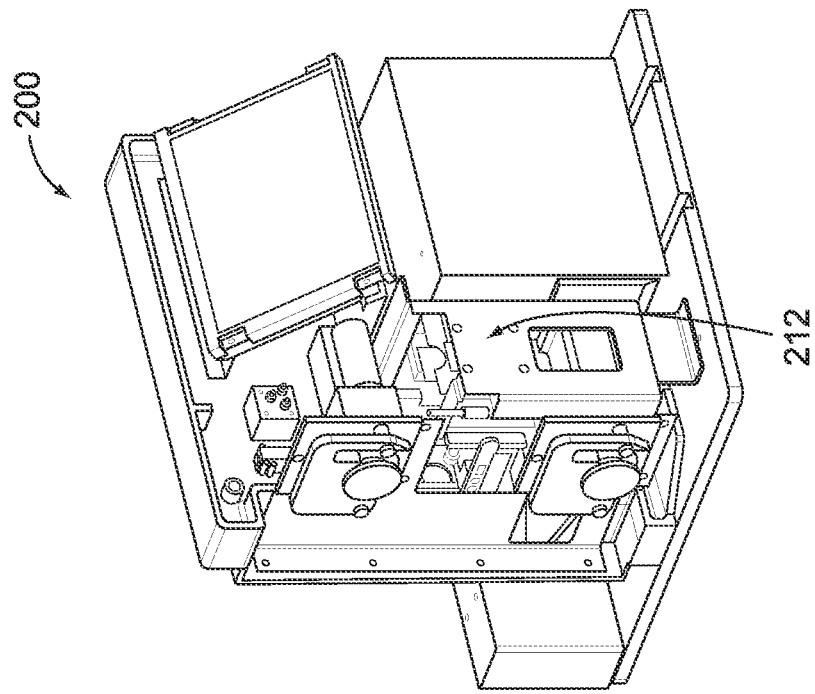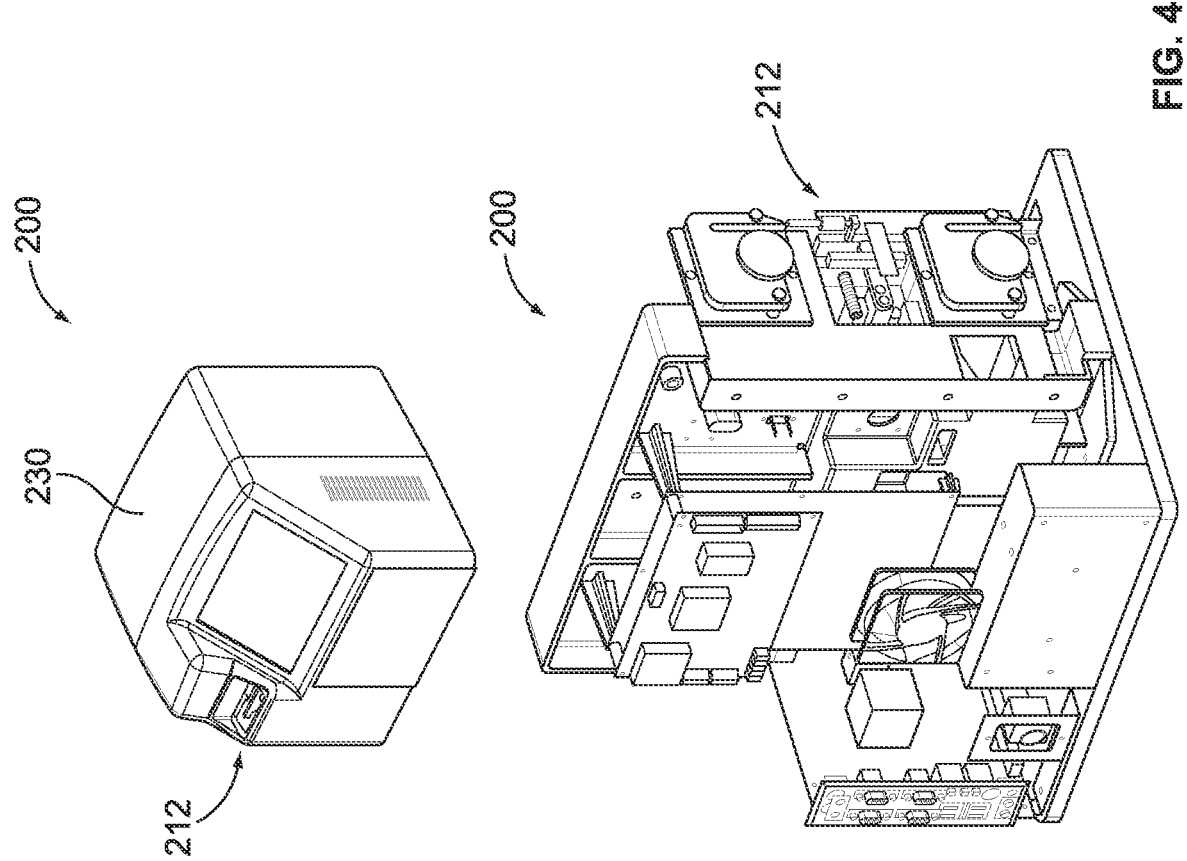
FIG. 4

MICRODEVICES AND BIOSENSOR CARTRIDGES FOR BIOLOGICAL OR CHEMICAL ANALYSIS AND SYSTEMS AND METHODS FOR THE SAME

CROSS REFERENCE TO RELATED APPLICATION

The present application is a continuation of U.S. application Ser. No. 16/529,397 ("the '397 Application"), filed Aug. 1, 2019, which is a continuation of U.S. application Ser. No. 15/936,165 ("the '165 Application"), filed Mar. 26, 2018, which is a divisional of U.S. application Ser. No. 15/205,275 ("the '275 Application"), filed Jul. 8, 2016, which is a continuation of U.S. application Ser. No. 14/729,809 ("the '809 Application"), filed Jun. 3, 2015, now U.S. Pat. No. 9,387,476, which is a continuation-in-part of U.S. application Ser. No. 13/882,088 ("the '088 Application"), filed Apr. 26, 2013, now U.S. Pat. No. 9,096,899, which is a National Stage of International Application No. PCT/US2011/057111, filed Oct. 20, 2011, which claims the benefit of U.S. Provisional Application Ser. No. 61/407,350 ("the '350 Application"), filed Oct. 27, 2010. Each of the aforementioned applications is incorporated herein by reference in its entirety.

STATEMENT REGARDING FEDERALLY SPONSORED RESEARCH OR DEVELOPMENT

This invention was made with Government support under NIH Grant Number HG003571 awarded by the PHS. The Government has certain rights in the invention.

BACKGROUND OF THE INVENTION

Embodiments of the present invention relate generally to biological or chemical analysis and more particularly, to systems and methods using microfluidic and detection devices for biological or chemical analysis.

Various protocols in biological or chemical research involve performing a large number of controlled reactions on local support surfaces or within predefined reaction chambers. The desired reactions may then be observed or detected, and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Other examples of such protocols include known DNA sequencing processes, such as sequencing-by-synthesis or cyclic-array sequencing. In cyclic-array sequencing, a dense array of DNA features (e.g., template nucleic acids) are sequenced through iterative cycles of enzymatic manipulation. After each cycle, an image may be captured and subsequently analyzed with other images to determine a sequence of the DNA features.

As a more specific example, one known DNA sequencing system uses a pyrosequencing process and includes a chip having a fused fiber-optic faceplate with millions of wells. A single capture bead having clonally amplified sstDNA from a genome of interest is deposited into each well. After the capture beads are deposited into the wells, nucleotides are sequentially added to the wells by flowing a solution containing a specific nucleotide along the faceplate. The environment within the wells is such that if a nucleotide flowing through a particular well complements the DNA strand on the corresponding capture bead, the nucleotide is added to the DNA strand. Incorporation of the nucleotide into the DNA strand initiates a process that ultimately generates a chemiluminescent light signal. The system includes a CCD camera that is positioned directly adjacent to the faceplate and is configured to detect the light signals from the wells. Subsequent analysis of the images taken throughout the pyrosequencing process can determine a sequence of the genome of interest.

However, the above pyrosequencing system, in addition to other systems, may have certain limitations. For example, the fiber-optic faceplate is acid-etched to make millions of small wells. Although the wells may be approximately spaced apart from each other, it is difficult to know a precise location of a well in relation to other adjacent wells. When the CCD camera is positioned directly adjacent to the faceplate, the wells are not evenly distributed along the pixels of the CCD camera and, as such, the wells are not aligned in a known manner with the pixels. Inter-well crosstalk between the adjacent wells makes distinguishing true light signals from the well of interest from other unwanted light signals difficult in the subsequent analysis. As a result, data recorded during the sequencing cycles must be carefully analyzed. Furthermore, the above system uses a high-resolution camera (16 Megapixels) to determine true signals from unwanted crosstalk. However, the high-resolution camera generates large amounts of data that must be analyzed that, in turn, may slow down the process. The high-resolution camera can also be expensive.

Furthermore, the above pyrosequencing system may use a number of enzymatic strategies to reduce crosstalk. For example, the system may use apyrase to degrade unincorporated nucleotide species and ATP, exonuclease to degrade linear nucleic acid molecules, pyrophosphatase (also referred to as PPi-ase) to degrades PPi, and/or enzymes to inhibit activity of other enzymes. However, these enzymatic strategies may increase the total costs of sequencing and may also negatively affect the system's ability to discern the true light signals for a certain well.

Moreover, sequencing systems and other bioassay systems must fluidicly deliver reagents and enzymes to the wells or other reaction sites and remove the unused reagents and enzymes. Some challenges that arise in delivering/removing the reagents and enzymes include bubble formation within a fluidic system. Bubbles disrupt the flow of the fluids through the faceplate as well as negatively affect the imaging of a reaction sites. Furthermore, if a system does not have uniform flow through the faceplate, then some wells may not be properly washed or may receive the reagents at different times or in different concentrations with respect to other wells in the chip. This may lead to misleading or incorrect data.

Bioassay systems are also typically configured to perform only one assay protocol or very similar protocols. For example, the CCD camera in the pyrosequencing system described above may have unique features and be configured to detect light signals emitted from the wells of the faceplate. However, the features and predetermined configuration of the CCD camera may not be suitable for other types of sequencing protocols or other assay protocols. As such, the system may be limited to only those protocols that require the CCD camera to be predisposed in a similar way.

In addition to the above challenges and limitations, there is a general need for more user-friendly bioassay systems that reduce costs relative to other known systems and also increase control and efficiency of the reactions intended to be observed.

BRIEF DESCRIPTION OF THE INVENTION

In accordance with one embodiment, a biosensor cartridge configured to engage a bioassay system is provided. The biosensor cartridge includes a flow cell having inlet and outlet ports and a flow channel that extends therebetween. The flow cell can include a substrate field comprising a plurality of reaction chambers. The reaction chambers have apertures that open onto the flow channel such that the reaction chambers are in fluid communication with the flow channel. The biosensor cartridge can also include an activity detector that is coupled to the flow cell and has an array of pixels that have a fixed positioned relative to the substrate field. The pixels may be assigned to select reaction chambers such that activity detected by the pixels indicates that a desired reaction has occurred within the select reaction chamber. The biosensor cartridge also includes an exterior side surface that has a plurality of electrical contacts thereon that are communicatively coupled to the pixels. The electrical contacts of the side surface are configured to engage corresponding mating contacts of a bioassay system.

In another embodiment, a biosensor cartridge that is configured to removably engage a bioassay system is provided. The biosensor cartridge includes a flow cell having inlet and outlet ports and a flow channel that extends therebetween. The biosensor cartridge also includes an activity detector that is coupled to the flow cell and is configured to detect activity along the flow channel that is indicative of desired reactions. The biosensor cartridge may also have first and second side surfaces. The first side surface can include the inlet and outlet ports. The second side surface can include electrical contacts that are communicatively coupled to the activity detector. The first and second side surfaces may face in substantially opposite directions.

In yet another embodiment, a flow cell is provided that includes inlet and outlet ports in fluid communication with each other through a flow channel that extends therebetween. The flow channel has a diffuser region and a field region that is located downstream from the diffuser region. The field region of the flow channel directs fluid along reaction sites where desired reactions occur. The fluid flows through the diffuser region in a first flow direction and through the field region in a second flow direction. The first and second flow directions can be substantially perpendicular to each other.

In a further embodiment, a workstation for biological or chemical analysis is provided. The workstation includes a receptacle that is configured to receive and establish electrical and fluidic couplings with a microdevice and a fluidic control system for controlling a flow of fluid through the microdevice. The fluidic control system includes an upstream conduit for delivering the fluid and a downstream conduit for removing the fluid. The workstation also includes a user interface that is configured to receive user selections or inputs and a system controller that includes an identification module and a protocol module. The identification module is configured to receive signals relating to identification information of the microdevice. The protocol module is configured to determine at least one parameter of an assay protocol based at least in part on the identification information. An operation of the fluidic control system is based at least in part on the determined at least one parameter.

In another embodiment, a system receptacle that is configured to engage a biosensor cartridge is provided. The system receptacle includes an alignment assembly that is configured to hold the biosensor cartridge in a predetermined orientation. The system receptacle also includes an upstream conduit for delivering fluid to the biosensor cartridge and a downstream conduit for removing the fluid from the biosensor cartridge. The upstream and downstream conduits include respective nozzles. The system receptacle also includes an actuation device that is configured to move the nozzles of the upstream and downstream conduits toward the biosensor cartridge in an axial direction to establish a fluidic connection.

In a further embodiment, a workstation for biological or chemical analysis is provided. The workstation includes a workstation housing and a fluidic-control system at least partially positioned within the housing. The fluidic-control system includes an upstream conduit for delivering fluid to a biosensor cartridge and a downstream conduit for removing the fluid from the biosensor cartridge. The system receptacle is configured to receive the biosensor cartridge. The system receptacle includes an alignment assembly that is configured to hold the biosensor cartridge in a predetermined orientation and upstream and downstream nozzles fluidicly coupled to the upstream and downstream conduits, respectively. The system receptacle also includes an actuation device that is configured to move the nozzles of the upstream and downstream conduits toward the alignment assembly in an axial direction to establish a fluidic connection with the biosensor cartridge.

In yet another embodiment, a reservoir bag is provided that has top and bottom ends and a height extending therebetween. A gravitational force direction is configured to extend from the top end to the bottom end when the reservoir bag is in operation. The reservoir bag includes at least one flexible wall that defines a variable volume for holding a fluid. The volume has a main storage portion, a flow path portion, and a bridge portion. The main storage portion and the flow path portion are in fluid communication with each other through the bridge portion. The reservoir bag also includes a bag opening that is located proximate to the top end. The fluid flowing through the bag opening when the fluid is removed. The reservoir bag also includes a partition that projects from the top end toward the bottom end to a distal tip and separates the main storage and flow path portions. The bridge portion is located between the distal tip and the bottom end.

In one embodiment, a bioassay system is provided that is configured to engage a microdevice for performing desired reactions and detecting activity that is indicative of the desired reactions. The bioassay system includes a system receptacle configured to engage the microdevice and a fluidic-control system that is configured to control a flow of fluid through the microdevice. The fluidic-control system is in fluid communication with the microdevice. The bioassay system also includes a fluid storage system that is fluidicly coupled to the fluidic-control system. The fluid storage system is configured to provide reagents to be used for the desired reactions within the microdevice. The bioassay system also includes a temperature control system and a user interface that is configured to receive user inputs from a user of the bioassay system. Furthermore, the bioassay system includes a system controller that is configured to control operation of the fluidic-control, the fluid storage, and the temperature control systems. The system controller is also configured to receive the user inputs from the user interface. The user inputs may relate to an assay protocol to run when the microdevice is engaged. The system controller may also communicate detection data to the user interface. The user interface can display the detection data to the user.

In another embodiment, a method of manufacturing a biosensor cartridge is provided. The method comprises providing a base substrate including an activity detector that has an array of pixels and circuitry for communicating data regarding activity detected by the pixels. The base substrate has an exterior side surface that includes a plurality of electrical contacts thereon that are communicatively coupled to the pixels through the circuitry. The method also includes mounting a substrate layer over the array of pixels. The substrate layer can include a plurality of reaction chambers where desired reactions are conducted. The substrate layer is mounted over the array of pixels such that the pixels are assigned to select reaction chambers. Activity detected by the assigned pixels indicates that a desired reaction has occurred within the select reaction chamber.

In yet another embodiment, a method of conducting an assay protocol using directed condensation is provided. The method includes providing a flow cell that has a flow channel and a substrate layer having a plurality of reaction chambers therein that are in fluid communication with the flow channel. The flow cell includes a cover wall that is spaced apart from the substrate layer. The cover wall separates the flow channel and an exterior side surface. The flow channel directs a flow of fluid between the cover wall and the substrate layer. The method also includes interfacing a thermal element with an engagement area of the side surface. The thermal element is configured to transfer or absorb thermal energy of the fluid in the flow channel through the cover wall. The method also includes providing thermal energy to the fluid within the flow channel during an assay protocol. The thermal energy is absorbed by the fluid within the flow channel and transferred to the fluid within the reaction chambers.

In another embodiment, a method of amplifying and sequencing DNA within a flow cell is provided. The method includes providing a flow cell that has a flow channel and a substrate layer having a plurality of reaction chambers therein that are in fluid communication with the flow channel. The flow cell includes a cover wall that is spaced apart from the substrate layer and defines the flow channel therebetween. The flow channel directs a flow of fluid between the cover wall and the substrate layer. The reaction chambers include DNA samples therein. The method also includes flowing a first aqueous solution that includes at least one of reagents and enzymes for DNA amplification through the flow channel. The method also includes flowing a non-polar liquid through the flow channel such that the first aqueous solution is substantially removed from the flow channel. The reaction chambers include the first aqueous solution therein that interfaces with the non-polar liquid in the flow channel. The method also includes controlling a temperature of the first aqueous solution in the reaction chambers to perform DNA amplification and flowing a second aqueous solution through the flow channel to remove the first aqueous solution. Furthermore, the method includes flowing a third aqueous solution through the flow channel that includes at least one of reagents and enzymes for DNA sequencing.

BRIEF DESCRIPTION OF THE DRAWINGS

FIG. 4 provides perspective views of the workstation of FIG. 3.

DETAILED DESCRIPTION OF THE INVENTION

Figure 1:
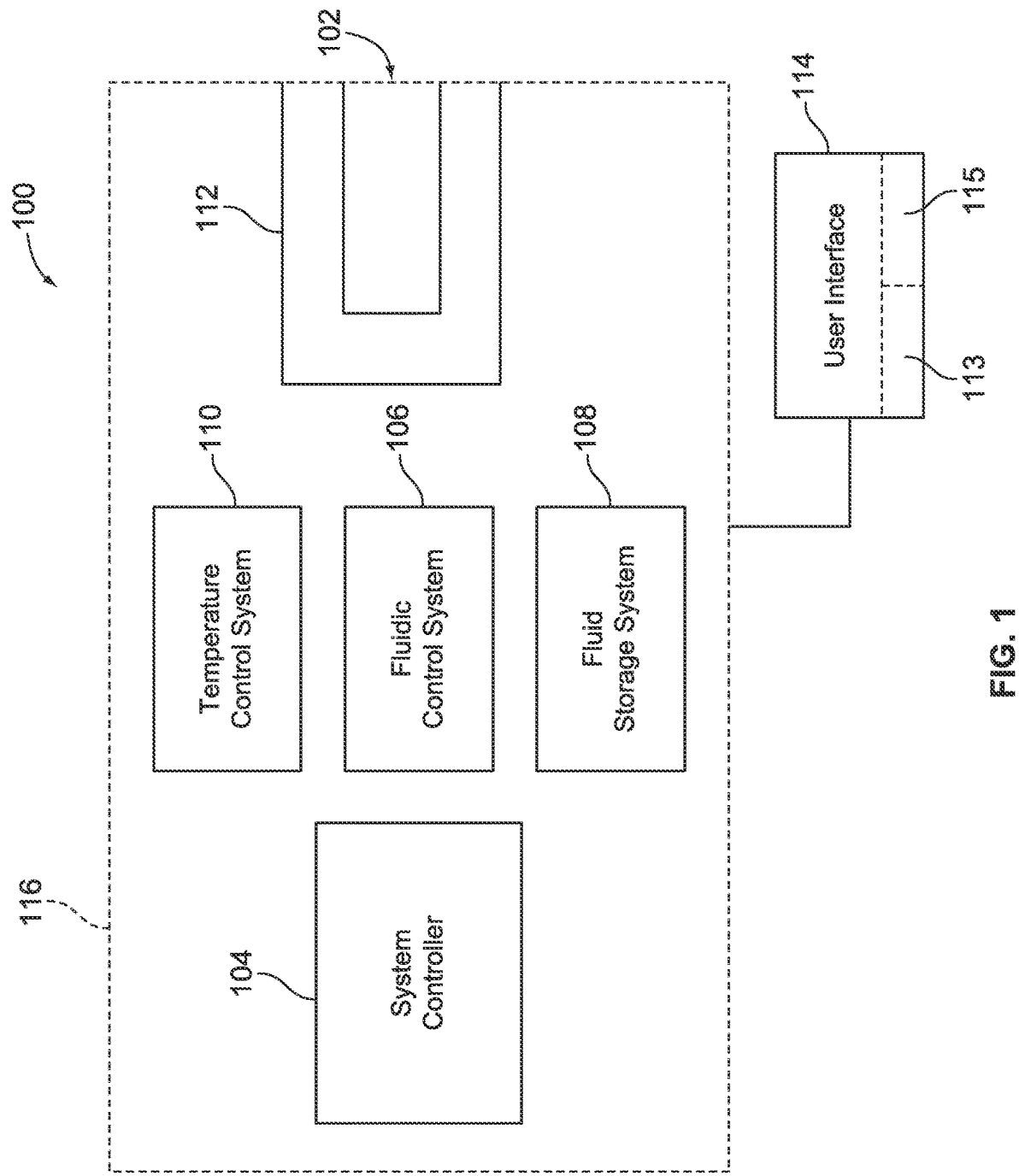
FIG. 1 is a block diagram of a system for biological or chemical analysis formed in accordance with one embodiment.

Embodiments described herein may be used in various biological or chemical processes and systems for academic or commercial analysis. More specifically, embodiments described herein may be used in various processes and systems where it is desired to detect an event, property, quality, or characteristic that is indicative of a desired reaction. For example, embodiments described herein include biosensor cartridges, microdevices, and their components as well as bioassay systems that operate with the biosensor cartridges and microdevices. In particular embodiments, the biosensor cartridges and microdevices include a flow cell and an activity detector that are coupled together in a substantially unitary structure.

The bioassay systems may be configured to perform a plurality of desired reactions that may be detected individually or collectively. The microdevices and bioassay systems may be configured to perform numerous cycles where the plurality of desired reactions occur in parallel. For example, the bioassay systems may be used to sequence a dense array of DNA features through iterative cycles of enzymatic manipulation and image acquisition. As such, the biosensor cartridges and microdevices may include one or more microfluidic channels that deliver reagents or other reaction components to a reaction site. In some embodiments, the reaction sites are reaction chambers that compartmentalize the desired reactions therein. Furthermore, embodiments may include an activity detector that is configured to detect activity that is indicative of the desired reactions.

As used herein, a "desired reaction" includes a change in at least one of a chemical, electrical, physical, and optical property or quality of a substance that is in response to a stimulus. For example, the desired reaction may be a chemical transformation, chemical change, or chemical interaction. The desired reaction may also be a change in electrical properties. For example, the desired reaction may be a change in ion concentration within a solution. Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The desired reaction can also be addition or elimination of a proton, for example, detectable as a change in pH of a surrounding solution or environment.

The stimulus can be at least one of physical, optical, electrical, magnetic, and chemical. For example, the stimulus may be an excitation light that excites fluorophores in a substance. The stimulus may also be a change in a surrounding environment, such as a change in concentration of certain biomolecules (e.g., enzymes or ions) in a solution. The stimulus may also be an electrical current applied to a solution within a predefined volume. In addition, the stimulus may be provided by shaking, vibrating, or moving a reaction chamber where the substance is located to create a force (e.g., centripetal force). As used herein, the phrase "in response to a stimulus" is intended to be interpreted broadly and include more direct responses to a stimulus (e.g., when a fluorophore emits energy of a specific wavelength after absorbing incident excitation light) and more indirect responses to a stimulus in that the stimulus initiates a chain of events that eventually results in the response (e.g., incorporation of a base in pyrosequencing eventually resulting in chemiluminescence). The stimulus may be immediate (e.g., excitation light incident upon a fluorophore) or gradual (e.g., change in temperature of the surrounding environment).

As used herein, the phrase "activity that is indicative of a desired reaction" and grammatical variants thereof include any detectable event, property, quality, or characteristic that may be used to facilitate determining whether a desired reaction has occurred. For example, the detected activity may be a light signal generated in fluorescence or chemiluminescence. The detected activity may also be a change in electrical properties of a solution within a predefined volume or along a predefined area. The detected activity may be a change in temperature.

As used herein, a "reaction component" or "reactant" includes any substance that may be used to obtain a desired reaction. For example, reaction components include reagents, enzymes, samples, other biomolecules, and buffer solutions. The reaction components are typically delivered to a reaction site in a solution or immobilized within a reaction site. The reaction components may interact directly or indirectly with the substance of interest.

As used herein, the term "reaction site" is a localized region where a desired reaction may occur. A reaction site may include support surfaces of a substrate where a substance may be immobilized thereon. For example, a reaction site may include a substantially planar surface in a channel of a flow cell that has a colony of clonally amplified sstDNA thereon. Furthermore, a plurality of reactions sites may be arranged side-by-side in a matrix, such as in microarrays. A reaction site can also include a reaction chamber that at least partially defines a spatial region or volume configured to compartmentalize the desired reaction. As used herein, the term "reaction chamber" includes a spatial region that is in fluid communication with a flow channel. The reaction chamber may be at least partially separated from the surrounding environment or other spatial regions. For example, a plurality of reaction chambers may be separated from each other by shared walls. As a more specific example, the reaction chamber may include a cavity defined by interior surfaces of a well and have an opening or aperture so that the cavity may be in fluid communication with a flow channel.

In some embodiments, the reaction chambers are sized and shaped relative to solids (including semi-solids) so that the solids may be inserted, fully or partially, therein. For example, the reaction chamber may be sized and shaped to accommodate only one capture bead. The capture bead may have clonally amplified DNA or other substances thereon. Alternatively, the reaction chamber may be sized and shaped to receive an approximate number of beads or solid substrates. As another example, the reaction chambers may also be filled with a porous gel or substance that is configured to control diffusion or filter fluids that may flow into the reaction chamber.

As used herein, a "substance" includes items or solids, such as capture beads, as well as biological or chemical substances. As used herein, a "biological or chemical substance" includes biomolecules, samples of interest, and other chemical compound(s). A biological or chemical substance may be used to detect, identify, or analyze other chemical compound(s), or function as intermediaries to study or analyze other chemical compound(s). In particular embodiments, the biological or chemical substances include a biomolecule. As used herein, a "biomolecule" includes at least one of nucleosides, nucleic acids, polynucleotides, oligonucleotides, proteins, enzymes, polypeptides, antibodies, antigens, ligands, receptors, polysaccharide, carbohydrate, polyphosphates cells, tissues, organisms, and any other biologically active chemical compound(s) such as analogs or mimetics of the aforementioned species.

In a further example, a biological or chemical substance or a biomolecule includes an enzyme or reagent used in a coupled reaction to detect the product of another reaction such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated herein in its entirety.

Biomolecules, samples, and biological or chemical substances may be naturally occurring or synthetic and may be suspended in a solution or mixture within a spatial region. Biomolecules, samples, and biological or chemical substances may also include a pharmaceutical composition. In some cases, biomolecules, samples, and biological or chemical substances of interest may be referred to as targets, probes, or analytes.

As used herein, a "microdevice" and a "biosensor cartridge" include a structure having a plurality of the reaction sites. A microdevice or a biosensor cartridge may include at least one of a flow channel and an electrical circuit. For example, a microdevice or a biosensor cartridge may include at least one flow channel that is in fluid communication with the reaction sites. As such, the microdevice or biosensor cartridge may be referred to as a microfluidic device. In some embodiments, the biosensor cartridge includes a microdevice. For example, after the microdevice is prepared or manufactured, the microdevice may be coupled to a housing or container to form the biosensor cartridge. In some embodiments, the microdevices and the biosensor cartridges may be self-contained, disposable units. However, other embodiments may include an assembly with removable parts that allow a user to access an interior of the microdevice for maintenance or replacement of components or samples. The microdevice and the biosensor cartridge may be removably coupled or engaged to larger bioassay systems, such as a sequencing system, that conducts controlled reactions therein.

In particular embodiments, the microdevice or biosensor cartridge may include an activity detector. As used herein, an "activity detector" is any device or component that is capable of detecting the activity that is indicative of a desired reaction. An activity detector may be able detect predetermined events, properties, qualities, or characteristics within a predefined volume or area. For example, an activity detector may be able to capture an image of the predefined volume or area. An activity detector may be able detect an ion concentration within a predefined volume of a solution or along a predefined area. Exemplary activity detectors include charged-coupled devices (CCD's) (e.g., CCD cameras); photomultiplier tubes (PMT's); molecular characterization devices or detectors, such as those used with nanopores; microcircuit arrangements, such as those described in U.S. Pat. No. 7,595,883, which is incorporated herein by reference in the entirety; and CMOS-fabricated sensors having field effect transistors (FET's), including chemically sensitive field effect transistors (chemFET), ion-sensitive field effect transistors (ISFET), and/or metal oxide semiconductor field effect transistors (MOSFET).

However, in other embodiments, the microdevice or biosensor cartridge does not include the activity detector. Such microdevices or biosensor cartridges may include flow cells that are configured to be positioned adjacent to an activity detector. For example, the microdevice may be a flow cell that is positioned directly adjacent to a CCD camera.

As used herein, when the terms "removably" and "coupled" (or "engaged") are used together to describe a relationship between the microdevice (or biosensor cartridge) and a system receptacle or interface of a bioassay system, the term is intended to mean that a connection between the microdevice and the system receptacle is readily separable without destroying the system receptacle. Accordingly, the microdevice may be removably coupled or engaged to the system receptacle in an electrical manner such that the mating contacts of the bioassay system are not destroyed. The microdevice may be removably coupled or engaged to the system receptacle in a mechanical manner such that the features that hold the microdevice are not destroyed. The microdevice may be removably coupled or engaged to the system receptacle in a fluidic manner such that the ports of the system receptacle are not destroyed. The system receptacle or a component is not considered to be "destroyed," for example, if only a simple adjustment to the component (e.g., realigning) or a simple replacement (e.g., replacing a nozzle) is required. However, in other embodiments where noted, the microdevice and the system receptacle may be readily separable without destroying either the microdevice or the system receptacle. Components are readily separable when the components may be separated from each other without undue effort or a significant amount of time spent in separating the components.

As used herein, the term "fluid communication" or "fluidicly coupled" refers to two spatial regions being connected together such that a liquid or gas may flow between the two spatial regions. For example, a microfluidic channel may be in fluid communication with a reaction chamber such that a fluid may flow freely into the reaction chamber from the microfluidic channel. The terms "in fluid communication" or "fluidicly coupled" allow for two spatial regions being in fluid communication through one or more valves, restrictors, or other fluidic components that are configured to control or regulate a flow of fluid through a system. In some cases, two spatial regions may be in fluid communication with each other even if, under certain conditions, a certain fluid would not be able to flow freely into a spatial region. For example, although a reaction chamber may be in fluid communication with a flow channel if the fluid were an aqueous solution, the interior surfaces of the reaction chamber may be modified or have certain properties that prevent the fluid from flowing into the reaction chamber when the fluid is a non-polar solution. For instance, the fluid may be oil and the interior surfaces of the reaction chamber may be hydrophilic.

As used herein, the term "immobilized," when used with respect to a biomolecule or biological or chemical substance, includes substantially attaching the biomolecule or biological or chemical substance at a molecular level to a surface. For example, biomolecule or biological or chemical substance may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to a surface of a substrate material may be based upon the properties of the substrate surface, the liquid medium carrying the biomolecule or biological or chemical substance, and the properties of the biomolecules or biological or chemical substances themselves. In some cases, a substrate surface may be first modified to have functional groups bound to the surface. The functional groups may then bind to biomolecules or biological or chemical substances to immobilize them thereon.

In some embodiments, nucleic acids can be attached to a surface and amplified using bridge amplification. Useful bridge amplification methods are described, for example, in U.S. Pat. No. 5,641,658; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein in its entirety. Another useful method for amplifying nucleic acids on a surface is rolling circle amplification (RCA), for example, using methods set forth in further detail below.

In particular embodiments, the assay protocols executed by the systems and methods described herein include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood however that non-natural nucleotides or analogs of the aforementioned nucleotides can be used. Some examples of useful non-natural nucleotides are set forth below in regard to reversible terminator-based sequencing by synthesis methods.

In some embodiments, items or solid substances (including semi-solid substances) may be disposed within the reaction chambers. When disposed, the item or solid may be physically held or immobilized within the reaction chamber through an interference fit, adhesion, or entrapment. Exemplary items or solids that may be disposed within the reaction chambers include polymer beads, pellets, agarose gel, powders, quantum dots, or other solids that may be compressed and/or held within the reaction chamber. In particular embodiments, a nucleic acid superstructure, such as a DNA ball, can be disposed in or at a reaction chamber, for example, by attachment to an interior surface of the reaction chamber or by residence in a liquid within the reaction chamber. A DNA ball or other nucleic acid superstructure can be preformed and then disposed in or at the reaction chamber. Alternatively, a DNA ball can be synthesized at the reaction chamber. A DNA ball can be synthesized by rolling circle amplification to produce a concatamer of a particular nucleic acid sequence and the concatamer can be treated with conditions that form a relatively compact ball. DNA balls and methods for their synthesis are described, for example in, U.S. Patent Publ. Nos. 2008/0242560 A1 or 2008/0234136 A1, each of which is incorporated herein in its entirety.

A substance that is held or disposed in a reaction chamber can be in a solid, liquid, or gaseous state. A substance can be held in a reaction chamber in the same state that it was introduced to the reaction chamber. For example, a liquid substance can be loaded into a reaction chamber and the substance can remain liquid whether or not it is converted to a different chemical species. Alternatively, a substance can be introduced to a reaction chamber in a first state and then converted to another state.

As used herein, an "environment" may be liquid, gas, or solid or a combination thereof. The environments in the reaction chambers and the flow channel may be different. As used herein, when the terms "separate" or "isolate" are used with respect to a surrounding environment and a substance within a reaction chamber, the substance may be separate from the surrounding environment without being completely isolated from the surrounding environment. For instance, a fluid in the flow channel may interface with, but not substantially intermix with through diffusion and the like, the environment or substance in the reaction chamber. By way of a more specific example, a hydrophilic solution within the reaction chamber may interface with a non-polar liquid that flows through the flow channel. In alternative embodiments, separation of a substance from a surrounding environment can be a fluidic isolation such that the substance in the reaction chamber is prevented from making physical contact with the surrounding environment. For example, a reaction chamber may be capped or sealed.

The reaction chambers and flow channels may have microfluidic dimensions in which surface tension and cohesive forces of a liquid in the reaction chamber and the adhesive forces between the liquid and interior surfaces that define the reaction chamber can have a significant effect on the liquid therein. As understood by those skilled in the art, a liquid may have different wetting abilities to a solid surface depending upon the natures of the liquid and the solid surface. Wetting is a liquid's ability to spread along a solid surface. The wetting of a solid surface by a liquid is controlled by the intermolecular interactions of molecules along an interface between the two phases. If the adhesive forces are relatively greater than the cohesive forces, the wetting of the liquid to the surface is greater. If the cohesive forces are relatively greater than the adhesive forces, the wetting of the liquid to the surface is smaller. Embodiments may utilize the wetting abilities of a fluid during the course of an assay or other usage.

In embodiments utilizing aqueous or polar liquids, the interaction between the liquid and the solid surface can be characterized as hydrophobic or hydrophilic. As used herein, a solid surface is hydrophobic if it repels an aqueous or polar liquid. For example, a contact angle between the aqueous or polar liquid and the hydrophobic surface of the solid is typically greater than 90 degrees. A surface is hydrophilic if it is attracted to an aqueous or polar liquid. For example, a contact angle between the aqueous or polar liquid and the hydrophilic surface of the solid will typically be less than 90 degrees.

In other embodiments, a non-polar liquid, such as alkanes, oils, and fats, may be used as the liquid within the reaction chamber and/or as part of the surrounding environment. Non-polar liquids may be attracted to a surface that has a hydrophobic interaction with aqueous or polar liquids. Likewise, non-polar liquids are not attracted to a surface that has a hydrophilic interaction with aqueous or polar liquids. As such, hydrophobic and hydrophilic surfaces may be used with embodiments described herein to control the flow of liquids through portions of the flow channel or within the reaction chambers.

Other factors may affect the contact angle or the wetting of a liquid to a solid. For example, a purity of the liquid or whether a surfactant is used may affect the surface tension of the liquid and the molecular interactions along the solid-liquid interface. A purity of the solid or whether a coating is placed on the solid surface may affect the surface energy of a solid. Also, temperature of the environment, a composition of the surrounding air, and the roughness or smoothness of the surface may all affect the interactions between the liquid and the solid surface. As such, embodiments described herein may utilize these other factors for certain purposes.

FIG. 1 is a block diagram of a bioassay system 100 for biological or chemical analysis formed in accordance with one embodiment. The term "bioassay" is not intended to be limiting as the bioassay system 100 may operate to obtain any information or data that relates to at least one of a biological and chemical substance. In some embodiments, the bioassay system 100 is a workstation that may be similar to a bench-top device or desktop computer. For example, a majority of the systems and components for conducting the desired reactions can be within a common housing 116.

In particular embodiments, the bioassay system 100 is a nucleic acid sequencing system (or sequencer) configured for various applications, including de novo sequencing, resequencing of whole genomes or target genomic regions, and metagenomics. The sequencer may also be used for RNA analysis. By way of example, the bioassay system 100 may read, for example, 100,000 beads and at about a 400 bp read length. Furthermore, in some embodiments, the bioassay system 100 may amplify template nucleic acid before sequencing of the nucleic acid is initiated.

The bioassay system 100 is configured to interact with a microdevice (or biosensor cartridge) 102 to perform desired reactions within the microdevice 102. In particular embodiments, the bioassay system 100 is configured to perform massively parallel reactions within the microdevice 102. The microdevice 102 includes one or more reaction sites where desired reactions can occur. The reaction sites can be, for example, elongated channels, reaction chambers, or planar surfaces. The microdevice 102 includes a flow channel that receives fluid from the bioassay system 100 and directs the fluid toward the reaction sites. Optionally, the microdevice 102 is configured to engage a thermal element for transferring thermal energy into or out of the flow channel. Furthermore, in some embodiments, the microdevice 102 includes an activity detector for detecting activity that is indicative of the occurrence of one or more desired reactions.

The bioassay system 100 may include various components, assemblies, and systems (or sub-systems) that interact with each other to perform a predetermined method or assay protocol for biological or chemical analysis. For example, the bioassay system 100 includes a system controller 104 that may communicate with the various components, assemblies, and sub-systems of the bioassay system 100 and also the microdevice 102. The bioassay system 100 may also include a system receptacle or interface 112 that engages the microdevice 102; a fluidic control system 106 to control the flow of fluid throughout a fluid network of the bioassay system 100 and the microdevice 102; a fluid storage system 108 that is configured to hold all fluids that may be used by the bioassay system; and a temperature control system 110 that may regulate the temperature of the fluid in the fluid network, the fluid storage system 108, and/or the microdevice 102.

Also shown, the bioassay system 100 may include a user interface 114 that interacts with the user. For example, the user interface 114 may include a display 113 to display or request information from a user and a user input device 115 to receive user inputs. In some embodiments, the display 113 and the user input device 115 are the same device (e.g., touchscreen). As will be discussed in greater detail below, the bioassay system 100 may communicate with various components to perform the desired reactions. The bioassay system 100 may also be configured to analyze the detection data to provide a user with desired information.

The system controller 104 may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. The above examples are exemplary only, and are thus not intended to limit in any way the definition and/or meaning of the term system controller. In the exemplary embodiment, the system controller 104 executes a set of instructions that are stored in one or more storage elements, memories, or modules in order to at least one of obtain and analyze detection data. Storage elements may be in the form of information sources or physical memory elements within the bioassay system 100.

The set of instructions may include various commands that instruct the bioassay system 100 or microdevice 102 to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the bioassay system 100, processed in response to user inputs, or processed in response to a request made by another processing machine (e.g., a remote request through a communication link).

The system controller 104 may be connected to the microdevice 102 and the other components of the bioassay system 100 via communication links. The system controller 104 may also be communicatively connected to off-site systems or servers. The communication links may be hardwired or wireless. The system controller 104 may receive user inputs or commands, from the user interface 114. The user input device 115 may include a keyboard, mouse, a touch-screen panel, and/or a voice recognition system, and the like. Alternatively or in addition, the user input device 115 may also be the display 113.

The fluidic control system 106 includes a fluid network and is configured to direct and regulate the flow of one or more fluids through the fluid network. The fluid network may be in fluid communication with the microdevice 102 and the fluid storage system 108. For example, select fluids may be drawn from the fluid storage system 108 and directed to the microdevice 102 in a controlled manner, or the fluids may be drawn from the microdevice 102 and directed toward, for example, a waste reservoir in the fluid storage system 108. Although not shown, the fluidic control system 106 may include flow sensors that detect a flow rate or pressure of the fluids within the fluid network. The sensors may communicate with the system controller 104.

The temperature control system 110 is configured to regulate the temperature of fluids at different regions of the fluid network, the fluid storage system 108, and/or the microdevice 102. For example, the temperature control system 110 may include a thermocycler that interfaces with the microdevice 102 and controls the temperature of the fluid that flows along the reaction sites in the microdevice 102. The temperature control system 110 may also regulate the temperature of solid elements or components of the bioassay system 100 or the microdevice 102. Although not shown, the temperature control system 110 may include sensors to detect the temperature of the fluid or other components. The sensors may communicate with the system controller 104.

The fluid storage system 108 is in fluid communication with the microdevice 102 and may store various reaction components or reactants that are used to conduct the desired reactions therein. The fluid storage system 108 may also store fluids for washing or cleaning the fluid network and microdevice 102 and for diluting the reactants. For example, the fluid storage system 108 may include various reservoirs to store reagents, enzymes, other biomolecules, buffer solutions, aqueous, and non-polar solutions, and the like. Furthermore, the fluid storage system 108 may also include waste reservoirs for receiving waste products from the microdevice 102.

The system receptacle or interface 112 is configured to engage the microdevice 102 in at least one of a mechanical, electrical, and fluidic manner. The system receptacle 112 may hold the microdevice 102 in a desired orientation to facilitate the flow of fluid through the microdevice 102. The system receptacle 112 may also include electrical contacts that are configured to engage the microdevice 102 so that the bioassay system 100 may communicate with the microdevice 102 and/or provide power to the microdevice 102. Furthermore, the system receptacle 112 may include fluidic ports (e.g., nozzles) that are configured to engage the microdevice 102. In some embodiments, the microdevice 102 is removably coupled to the system receptacle 112 in a mechanical manner, in an electrical manner, and also in a fluidic manner.

In some embodiments, the bioassay system 100 may have interchangeable or swappable devices (e.g., plug-and-play). For example, the system receptacle 112 may be readily replaced or substituted with a different system receptacle. This may occur when a different type of microdevice 102 is desired to be used. Furthermore, the fluid storage system 108 may be a container that is readily separated from the fluid network and replaced by another container. This may occur when the fluid in the container is depleted, has expired, or a different container is required because a user of the bioassay system 100 desires to run a different assay protocol. Furthermore, the system controller 104 may have swappable devices (e.g., if the user desires to use the bioassay system 100 to execute a different assay protocol).

In addition, the bioassay system 100 may communicate remotely with other systems or networks. Detection data obtained by the bioassay system 100 may be stored in a remote database.

Figure 2:
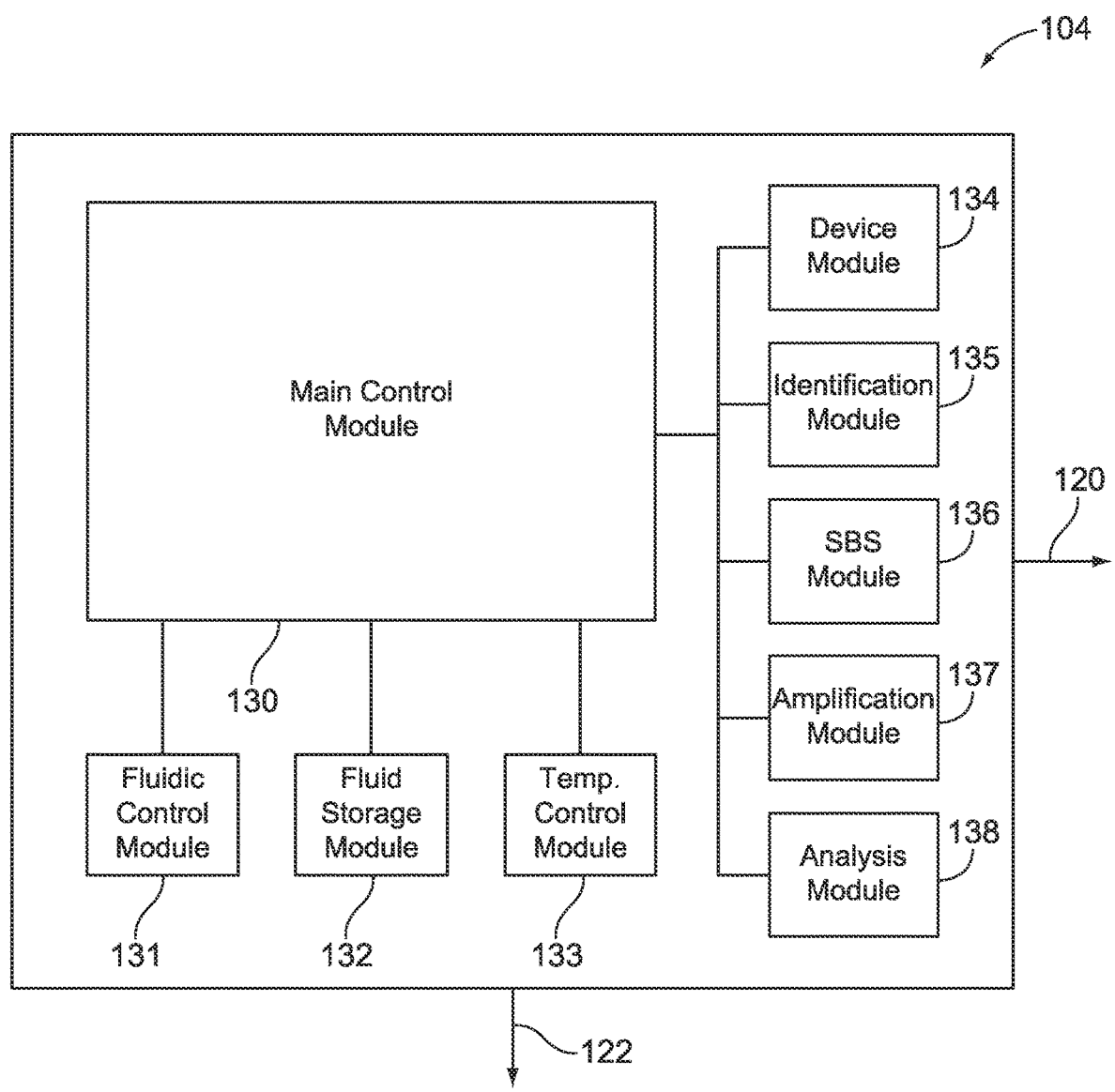
FIG. 2 is a block diagram of a system controller that may be used in the system of FIG. 1.

FIG. 2 is a block diagram of the system controller 104 in the exemplary embodiment. In one embodiment, the system controller 104 includes one or more processors or modules that can communicate with one another. The system controller 104 is illustrated conceptually as a collection of modules, but may be implemented utilizing any combination of dedicated hardware boards, DSPs, processors, etc. Alternatively, the system controller 104 may be implemented utilizing an off-the-shelf PC with a single processor or multiple processors, with the functional operations distributed between the processors. As a further option, the modules of described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication link 120 may transmit commands to or receive data from the microdevice 102 (FIG. 1) and/or the sub-systems 106, 108, 110 (FIG. 1). A communication link 122 may receive user input from the user interface 114 (FIG. 1) and transmit data or information to the user interface 114. Data from the microdevice 102 or sub-systems 106, 108, 110 may be processed by the system controller 104 in real-time during a bioassay session. Additionally or alternatively, data may be stored temporarily in a system memory during a bioassay session and processed in less than real-time or off-line operation.

The system controller 104 may include a plurality of modules 131-138 that communicate with a main control module 130. The main control module 130 may communicate with the user interface 114 (FIG. 1). Although the modules 131-138 are shown as communicating directly with the main control module 130, the modules 131-138 may also communicate directly with each other, the user interface 114, and the microdevice 102. Also, the modules 131-138 may communicate with the main control module 130 through the other modules.

The plurality of modules 131-138 include system modules 131-133 that communicate with the sub-systems 106, 108, and 110, respectively. The fluidic control module 131 may communicate with the fluidic control system 106 to control the valves and flow sensors of the fluid network for controlling the flow of one or more fluids through the fluid network. The fluid storage module 132 may notify the user when fluids are low or when the waste reservoir must be replaced. The fluid storage module 132 may also communicate with the temperature control module 133 so that the fluids may be stored at a desired temperature.

The plurality of modules 131-138 may also include a device module 134 that communicates with the microdevice 102 and an identification module 135 that determines identification information relating to the microdevice 102. The device module 134 may, for example, communicate with the system receptacle 112 to confirm that the microdevice has established an electrical and fluidic connection with the bioassay system 100. The identification module 135 may receive signals that identify the microdevice 102. The identification module 135 may use the identity of the microdevice 102 to provide other information to the user. For example, the identification module 135 may determine and then display a lot number, a date of manufacture, or a protocol that is recommended to be run with the microdevice 102.

The plurality of modules 131-138 may also include a detection data analysis module 138 that receives and analyzes the detection data (e.g., image data) from the microdevice 102. The processed detection data may be stored for subsequent analysis or may be transmitted to the user interface 114 to display desired information to the user.

Protocol modules 136 and 137 communicate with the main control module 130 to control the operation of the sub-systems 106, 108, and 110 when conducting predetermined assay protocols. The protocol modules 136 and 137 may include sets of instructions for instructing the bioassay system 100 to perform specific operations pursuant to predetermined protocols. The protocol modules 136 and 137 include a sequencing-by-synthesis (SBS) module 136 that may be configured to issue various commands for performing sequencing-by-synthesis processes. In some embodiments, the SBS module 136 may also process detection data.

By way of one example, the SBS module 136 may be configured to issue various commands for performing the steps of a pyrosequencing protocol. In this case, the microdevice 102 may include millions of wells where each well has a single capture bead having clonally amplified sstDNA thereon. Each well may also include other smaller beads that, for example, may carry immobilized enzymes (e.g., ATP sulfurylase and luciferase) or facilitate holding the capture bead in the well. The SBS module 136 may be configured to issue commands to the fluidic control module 106 to run consecutive cycles of fluids that carry a single type of nucleotide (e.g., 1st cycle: A; 2nd cycle: G; 3rd cycle: C; 4th cycle: T; 5th cycle: A; 6th cycle: G; 7th cycle: C; 8th cycle: T; and on). When a nucleotide is incorporated into the DNA, pyrophosphate is released thereby instigating a chain reaction where a burst of light is generated. The burst of light may be detected by an activity detector. Detection data may be communicated to the main control module 130, the detection data analysis module 138, and/or the SBS module 136 for processing. The detection data may be stored for later analysis or may be analyzed by the system controller 104 and an image may be sent to the user interface 114.

The SBS module 136 may also be configured to issue commands for other sequencing-by-synthesis processes. For example, the SBS module 136 may issue commands to perform bridge PCR where clusters of clonal amplicons are formed on localized areas within a channel (or lane) of a flow cell. After generating the amplicons through bridge PCR, the amplicons may be "linearized" to make sstDNA and a sequencing primer may be hybridized to a universal sequence that flanks a region of interest. For example, a reversible terminator-based sequencing by synthesis method can be used as follows. Each sequencing cycle extends the sstDNA by a single base and is accomplished by modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, an image in four channels is taken (i.e., one for each fluorescent label). After imaging, the fluorescent label and the terminator are chemically cleaved from the sstDNA. Another similar sequencing cycle may follow. In such a sequencing protocol, the SBS module 136 may instruct the fluidic control system 106 to direct a flow of reagent and enzyme solutions through the microdevice 102. Exemplary reversible terminator-based SBS methods which can be utilized with the apparatus and methods set forth herein are described in US Patent Application Publication No. 2007/0166705 A1, US Patent Application Publication No. 2006/0188901 A1, U.S. Pat. No. 7,057,026, US Patent Application Publication No. 2006/0240439 A1, US Patent Application Publication No. 2006/0281109 A1, PCT Publication No. WO 05/065814, US Patent Application Publication No. 2005/0100900 A1, PCT Publication No. WO 06/064199 and PCT Publication No. WO 07/010251, each of which is incorporated herein by reference in its entirety. Exemplary reagents for reversible terminator-based SBS are described in U.S. Pat. Nos. 7,541,444; 7,057,026; 7,414,116; 7,427,673; 7,566,537; 7,592,435 and WO 07/135368, each of which is incorporated herein by reference in its entirety.

The plurality of protocol modules may also include an amplification module 137 that is configured to issue commands to the fluidic control system 106 and the temperature control system 110 for amplifying a product within the microdevice 102. For example, the microdevice 102 may be engaged to the bioassay system 100. The bioassay system 100 may identify the type of microdevice or other information and automatically run an amplification protocol. Alternatively, the bioassay system 100 may request additional information from the user. The amplification module 137 may issue instructions to the fluidic control system 106 to deliver necessary amplification components to reaction chambers within the microdevice 102. The reaction chambers may already contain some components for amplification, such as the template DNA and/or primers. After delivering the amplification components to the reaction chambers, the amplification module 137 may instruct the temperature control system 110 to cycle through different temperature stages according to known amplification protocols.

In some embodiments, the amplification and SBS modules may operate in a single assay protocol where, for example, template nucleic acid is amplified and subsequently sequenced within the same biosensor cartridge.

In some embodiments, the user may provide user inputs through the user interface 114 to select an assay protocol to be run by the bioassay system 100. In other embodiments, the bioassay system 100 may automatically detect the type of microdevice 102 that has been inserted into the system receptacle 112 and confirm with the user the assay protocol to be run. Alternatively, the bioassay system 100 may offer a limited number of assay protocols that could be run with the determined type of microdevice 102. The user may select the desired assay protocol, and the bioassay system 100 may then perform the selected assay protocol based on preprogrammed instructions.

However, the bioassay system 100 may also allow the user to reconfigure an assay protocol. After determining the assay protocol to run, the bioassay system 100 may offer options to the user through the user interface 114 for modifying the determined protocol. For example, if it is determined that the microdevice 102 is to be used for amplification, the bioassay system 100 may request a temperature for the annealing cycle. Furthermore, the bioassay system 100 may issue warnings to a user if a user has provided user inputs that are generally not acceptable for the selected assay protocol.

Figure 3:
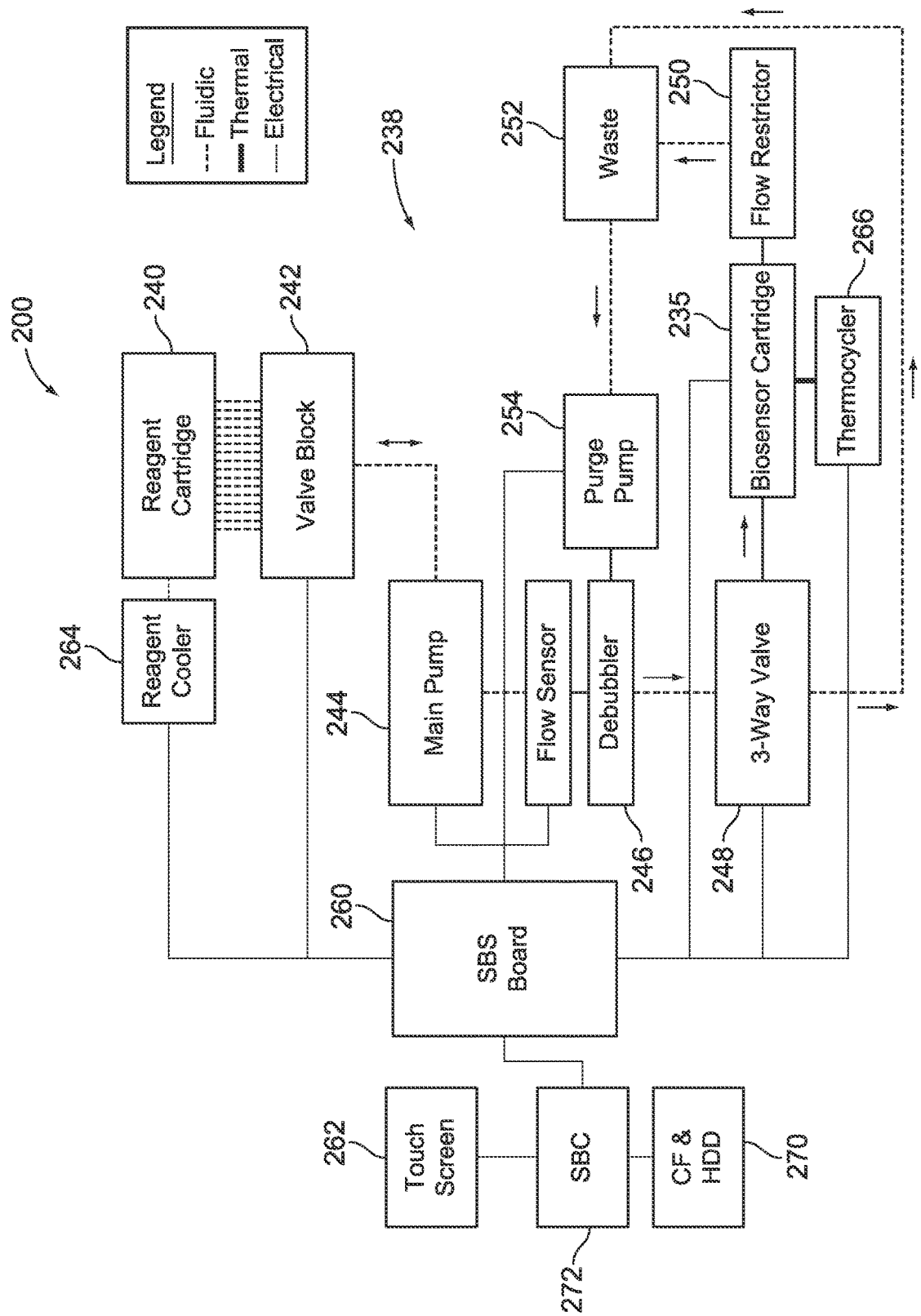
FIG. 3 is a block diagram of a workstation for biological or chemical analysis in accordance with one embodiment.

FIG. 3 is a block diagram of an exemplary workstation 200 for biological or chemical analysis in accordance with one embodiment. The workstation 200 may have similar features, systems, and assemblies as the bioassay system 100 described above. For example, the workstation 200 may have a fluidic control system, such as the fluidic control system 106 (FIG. 1), that is fluidically coupled to a biosensor cartridge or microdevice 235 through a fluid network 238. The fluid network 238 may include a reagent cartridge 240, a valve block 242, a main pump 244, a debubbler 246, a 3-way valve 248, a flow restrictor 250, a waste removal system 252, and a purge pump 254. In particular embodiments, most of the components or all of the components describe above are within a common workstation housing 230 (FIG. 4).

A flow of fluid is indicated by arrows along the fluid network 238. For example, reagent solutions may be removed from the reagent cartridge 240 and flow through the valve block 242. The valve block 242 may facilitate creating a zero-dead volume of the fluid flowing to the biosensor cartridge 235 from the reagent cartridge 240. The valve block 242 can select or permit one or more liquids within the reagent cartridge 240 to flow through the fluid network 238. For example, the valve block 242 can include 16 solenoid valves that have a compact arrangement. Each solenoid valve can control the flow of a fluid from a single reservoir bag. In some embodiments, the valve block 242 can permit two or more different liquids to flow into the fluid network 238 at the same time thereby mixing the two or more different liquids. After leaving the valve block 242, the fluid may flow through the main pump 244 and to the debubbler 246. The debubbler 246 is configured to remove unwanted gases that have entered or been generated within the fluid network 238.

From the debubbler 246, fluid may flow to the 3-way valve 248 where the fluid is either directed to the biosensor cartridge 235 or bypassed to the waste removal system 252. A flow of the fluid within the biosensor cartridge 235 may be at least partially controlled by the flow restrictor 250 located downstream from the biosensor cartridge 235. Furthermore, the flow restrictor 250 and the main pump 244 may coordinate with each other to control the flow of fluid across reaction sites and/or control the pressure within fluid network 238. Fluid may flow through the biosensor cartridge 235 and onto the waste removal system 252. Optionally, fluid may flow through the purge pump 254 and into, for example, a waste reservoir bag within the reagent cartridge 240.

Also shown in FIG. 3, the workstation 200 may include a temperature control system, such as the temperature control system 110, that is configured to regulate or control a thermal environment of the different components and sub-systems of the workstation 200. The temperature control system 110 can include a reagent cooler 264 that is configured to control a temperature of various fluids used by the workstation 200, and a thermocycler 266 that is configured to control a temperature of the biosensor cartridge 235. The thermocycler 266 can include a thermal element (not shown) that interfaces with the biosensor cartridge.

Furthermore, the workstation 200 may include a system controller or SBS board 260 that may have similar features as the system controller 104 described above. The SBS board 260 may communicate with the various components and sub-systems of the workstation 200 as well as the biosensor cartridge 235. Furthermore, the SBS board 260 may communicate with remote systems to, for example, store data or receive commands from the remote systems. The workstation 200 may also include a touch screen user interface 262 that is operatively coupled to the SBS board 260 through a single-board computer (SBC) 272. The workstation 200 may also include a compact-flash (CF) drive and/or a hard drive 270 for storing user data in addition to other software.

FIG. 4 provides various perspective views of the workstation 200. In particular embodiments, the workstation 200 is a stand-alone or bench-top unit such that all of the components described above with respect to FIG. 3 may be held within the workstation housing 230. However, in other embodiments, the workstation housing 230 may contain or partially contain only some of the components. The workstation 200 permits a user to perform desired reactions within the biosensor cartridge 235 (FIG. 3) and, optionally, perform primary analysis of obtained detection data of the desired reactions. The primary analysis may, for example, indicate to the user that the assay protocol was successfully run and provide preliminary results of the assay protocol. The user interface 262 may be configured to receive user inputs and commands as well as display information to the user. Also shown, the workstation 200 may also include a system receptacle 212 that is configured to receive and engage the biosensor cartridge 235.

Figure 5:
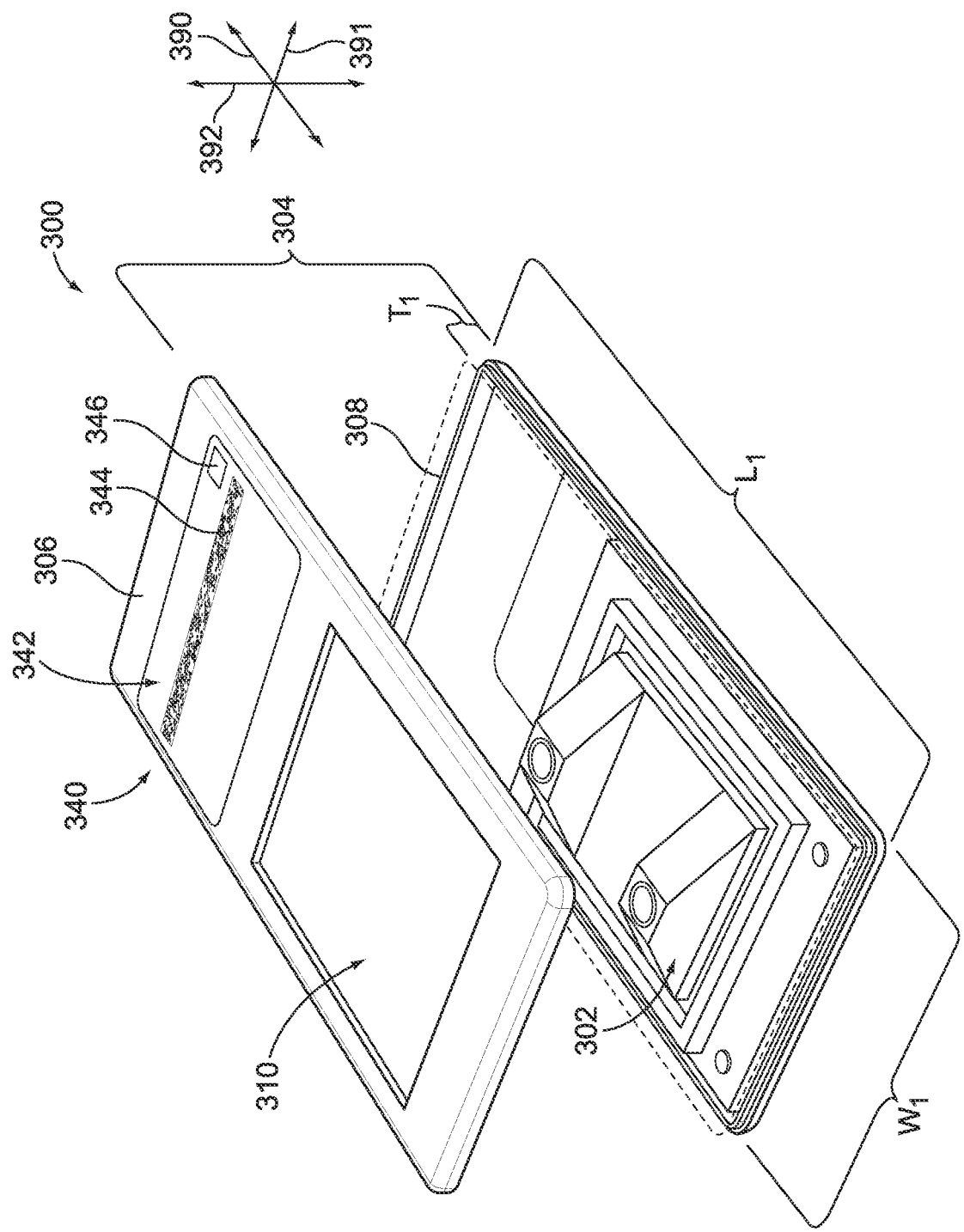
FIG. 5 is a partially exploded perspective view of a biosensor cartridge formed in accordance with one embodiment.
Figure 6:
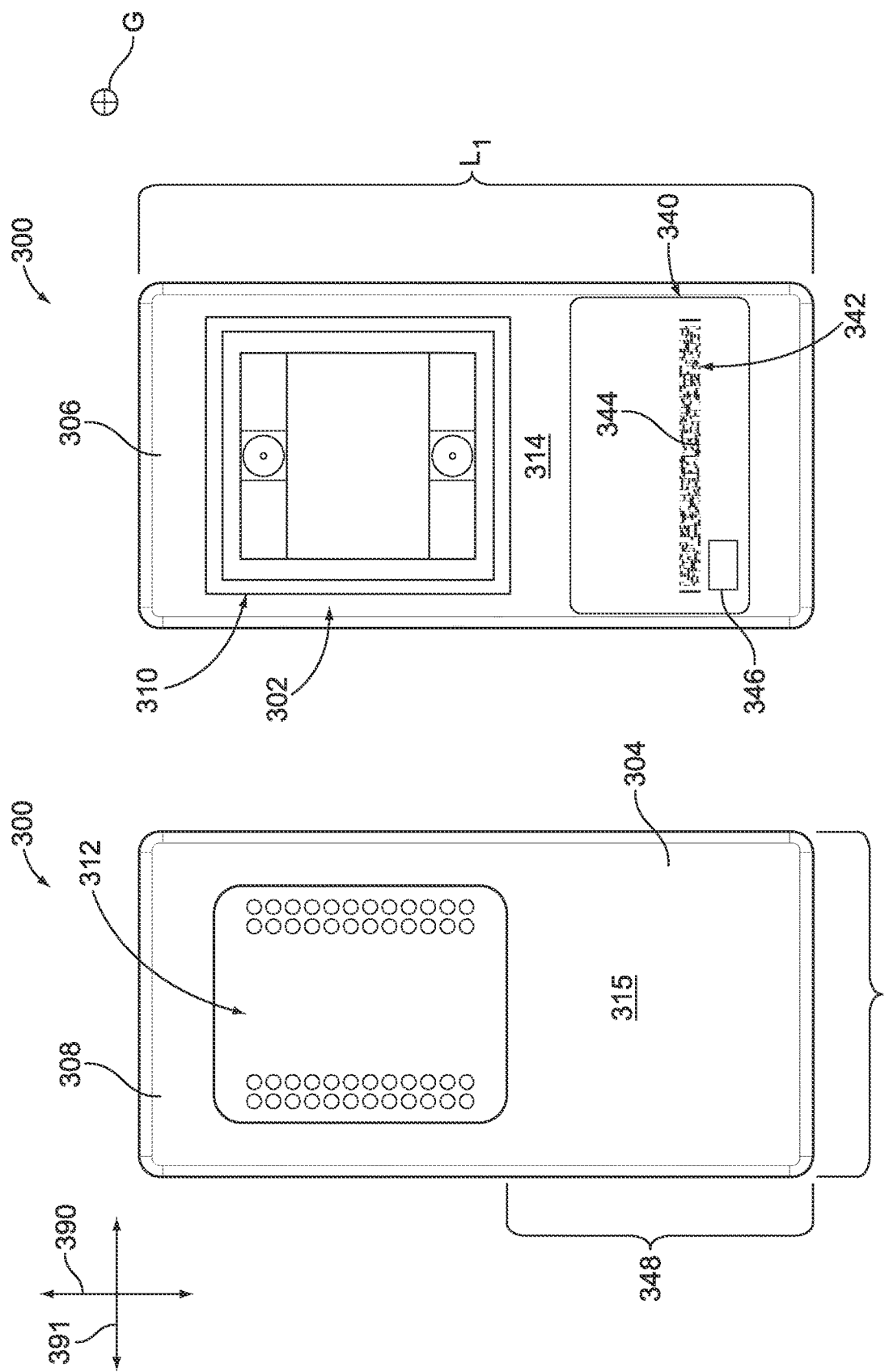
FIG. 6 shows plan views of the biosensor cartridge of FIG. 5.

FIGS. 5 and 6 illustrate a biosensor cartridge 300 formed in accordance with one embodiment that may be used with a bioassay system or workstation, such as the bioassay system 100 (FIG. 1) and the workstation 200 (FIG. 3). FIG. 5 is a partially exploded perspective view, and FIG. 6 provides plan views of opposite side surfaces 314 and 315 of the biosensor cartridge 300. As shown, the biosensor cartridge 300 is oriented with respect to a vertical or elevational axis 392 (FIG. 5) and lateral axes 390 and 391. In the illustrated embodiment, the biosensor cartridge 300 may include a microdevice 302. The biosensor cartridge 300 may also have a housing or casing 304 that encloses at least a portion of the microdevice 302. In the illustrated embodiment, the casing 304 may include opposite shells 306 and 308 that couple to each other along an interface. In some embodiments, the shells 306 and 308 are readily separated thereby allowing a user or a machine to replace components within the casing 304, such as the microdevice 302. For example, the shells 306 and 308 may form an interference fit (e.g., snap-fit) or slidably engage each other in a locking arrangement. The shells 306 and 308 may also use fasteners (e.g., screws or plugs) that removably couple the shells 306 and 308 together.

As shown, each of the shells 306 and 308 includes an opening or window 310 and 312 (FIG. 6), respectively, that is sized and shaped to provide access to the microdevice 302 therein or permit the microdevice 302 to project therethrough. As shown in FIG. 6, when the shells 306 and 308 are coupled together, the biosensor cartridge 300 may have exterior side surfaces 314 and 315. In the illustrated embodiment, the side surfaces 314 and 315 face in substantially opposite directions. For example, the side surfaces 314 and 315 may both face a direction along the vertical axis 392.

The biosensor cartridge 300 may be sized and shaped to facilitate handling by a user or machine and for being inserted into the system receptacle 212 (FIG. 4). For example, the biosensor cartridge may be substantially rectangular or card-shaped. The biosensor cartridge 300 may have a width $W_1$, a length $L_1$, and a thickness $T_1$ (as indicated by the dashed lines in FIG. 5). The width $W_1$, the length $L_1$, and the thickness $T_1$ along with other features of the casing 304 and the microdevice 302 may be configured to facilitate orienting the biosensor cartridge 300 when inserted into the system receptacle 212. The dimensions can be, for example, in a range of 1 cm to 50 cm, 1 cm to 25 cm, 1 cm to 10 cm, 5 cm to 50 cm, 5 cm to 25 cm, 5 cm to 10 cm, 10 cm to 50 cm or 10 cm to 25 cm. For example, the biosensor cartridge 300 or the casing 304 may have a tail end 348 (FIG. 6) that projects a substantial distance away from the microdevice 302 to allow a user or machine to grip the biosensor cartridge 300.

Figure 31:
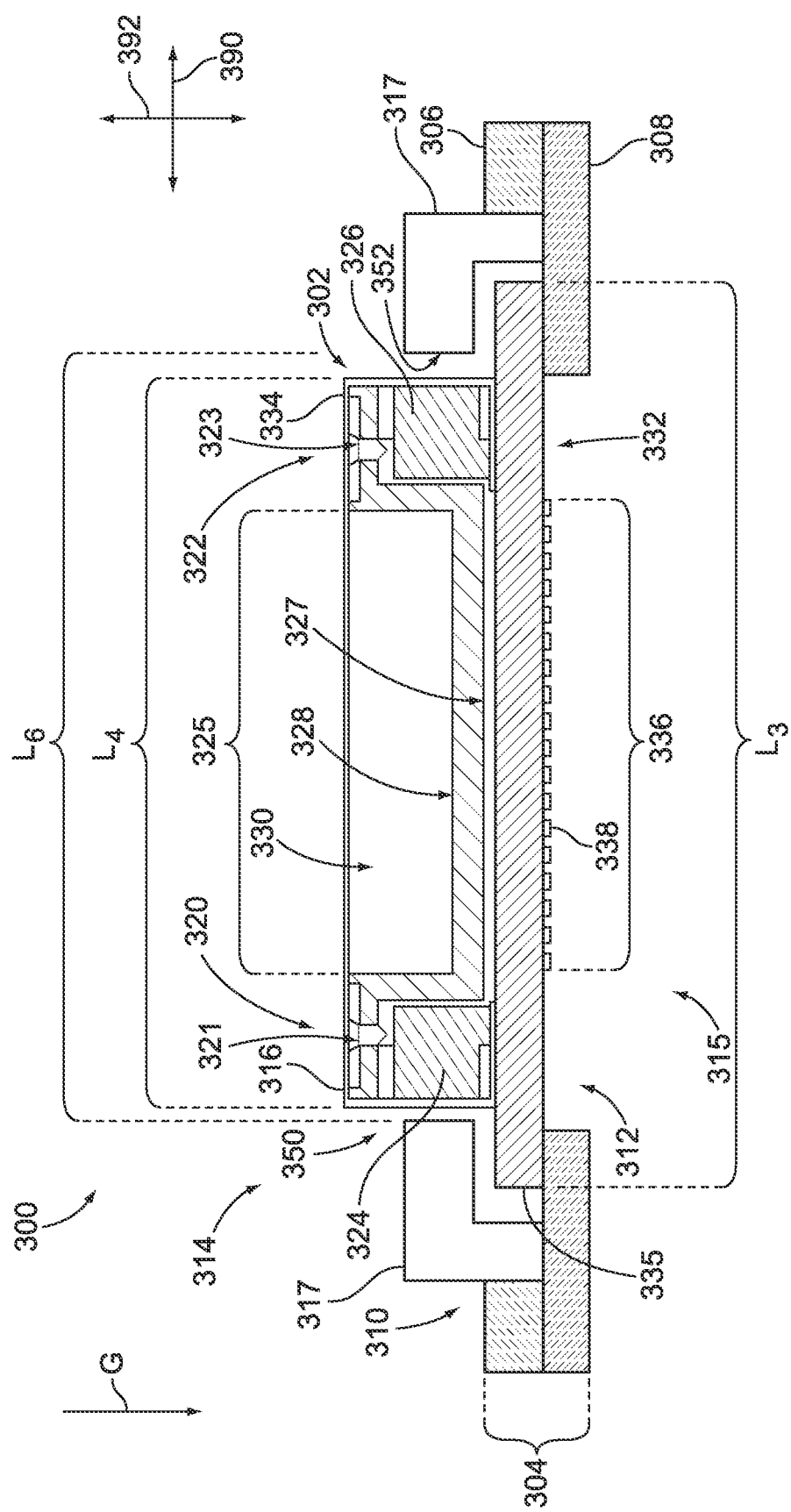
FIG. 31 is a cross-section of the biosensor cartridge shown in FIG. 5.

FIG. 31 is a cross-section of the biosensor cartridge 300. As shown, the microdevice 302 includes a device body 316 having opposite device side surfaces 330 and 332. The side surface 330 may be a portion of the side surface 314, and the side surface 332 may be a portion of the side surface 315. The device body 316 may include inlet and outlet ports 320 and 322 along the same side surface 330 of the device body 316. In alternative embodiments, the inlet and outlet ports 320 and 322 may be on opposite side surfaces. In other embodiments, at least one of the inlet and outlet ports 320 and 322 is located on an edge facing in a direction along the lateral axis 390 or the lateral axis 391 (FIG. 5). Also shown, the inlet and outlet ports 320 and 322 may have respective openings 321 and 323.

The microdevice 302 can include a flow cell 334 that is mounted to a base substrate 335. The base substrate 335 may be a printed circuit, such as a PCB, that includes conductive pathways therethrough. In alternative embodiments, the base substrate 335 is only configured to provide structural support to the flow cell 334. The flow cell 334 and the base substrate 335 may comprise the device body 316 and form a substantially unitary structure. As shown, the base substrate 335 comprises a planar body that may have lateral dimensions that are larger than the lateral dimensions of the flow cell 334. For example, the base substrate 335 may have a length $L_3$, and the flow cell 334 may have a length $L_4$. The length $L_3$ may be greater than the length $L_4$. When the flow cell 334 is mounted onto the base substrate 335, the flow cell 334 may be positioned such that the base substrate 335 extends beyond edges of the flow cell 334. Although not shown, the widths of the base substrate 335 and the flow cell 334 may be similarly sized and shaped with respect to each other.

Also shown, the device body 316 can be held within the casing 304 by a frame 317. The frame 317 may be attached to the casing 304 at the shell 308 or the shell 306. The frame 317 extends around at least a portion of a perimeter of the device body 316. In particular embodiments, the frame 317 completely surrounds the perimeter. The frame 317 may also define a window or opening 350 that is sized and shaped to permit the microdevice 302 (or the flow cell 334) to extend therethrough. The opening 350 may also block or prevent the base substrate 335 from moving therethrough. More specifically, the opening 350 may be defined by an interior edge 352 of the frame 317 and have a length $L_6$. The length $L_6$ may be less than the length $L_3$ of the base substrate 335.

In some embodiments the frame 317 holds the microdevice 302 in a substantially stationary position with respect to the case 304. However, in other embodiments, the microdevice 302 may be moveable or floatable within a restricted space defined by the biosensor cartridge 300. In such embodiments, the moveable or floatable quality of the microdevice 302 may permit the microdevice 302 to align with other components of the workstation 200 to facilitate fluidicly, thermally, and/or electrically engaging the workstation 200. For example, as shown in FIG. 31, interior surfaces of the frame 317 and the shell 308 may define a restricted space that has greater dimensions (e.g., length, height, and width) than the dimensions of the base substrate 335. In other words, the restricted space may provide additional spacing between the interior surfaces of the frame 317 and the shell 308. As such, the restricted space permits the microdevice 302 to shift and/or slightly rotate or pivot therein. For example, the microdevice 302 may be moveable in a lateral manner along a plane formed by the lateral axes 390, 391 (i.e., the microdevice may shift side-to-side). The microdevice also be moveable in a vertical manner along the vertical axis 392 (i.e., the microdevice may shift up-and-down). Furthermore, the microdevice 302 may also rotate or pivot about a vertical axis that extends through the microdevice 302 and/or rotate or pivot about a lateral axis that extends through the microdevice 302. Accordingly, the microdevice 302 may float with respect to the frame 317 or the casing 304.

However, the above description of the floatability of the microdevice 302 is exemplary only. The microdevice 302 and, more specifically, the device body 316 may have various structural features or other configurations that permit the microdevice 302 to float or move within a restricted space. Furthermore, in other embodiments, the microdevice 302 is held in a stationary or fixed position with respect to the casing 304.

Also shown in FIG. 31, the inlet and outlet ports 320 and 322 may be configured to removably engage nozzles of the workstation 200 to fluidicly couple a flow channel 327 of the biosensor cartridge 300 to the workstation 200. When in operation, fluid may flow through the microdevice 302 between the inlet and outlet ports 320 and 322 and respective openings 321 and 323. More specifically, the fluid may flow along the flow channel 327 within the biosensor cartridge 300 between the inlet and outlet portions 320 and 322. As shown, the inlet and outlet ports 320 and 322 may be separated from each other by a spacing 325. The spacing 325 may extend along and provide access to an engagement area 328 of the common side surface 330. The engagement area 328 may extend along and proximate to the flow channel within the biosensor cartridge 300.

As will be described in greater detail below, the engagement area 328 may be sized and shaped to interface with a thermal element of a thermocycler to facilitate controlling a temperature of the fluid within the microdevice 302. At least a portion of the engagement area 328 that extends along the flow channel may be a substantially flat surface. The engagement area 328 may extend along a lateral plane that is parallel to a plane formed by lateral axes 390 and 391. The side surface 332 may extend parallel to the engagement area 328.

As shown in FIG. 31, the device body 316 includes port projections 324 and 326 having the inlet and outlet ports 320 and 322. The port projections 324 and 326 may be separated from each other by the spacing 325 and the engagement area 328. The port projections 324 and 326 may project away from the casing 304 or the engagement area 328 in a substantially common direction (e.g., in a direction along the vertical axis 392). When oriented in the system receptacle 212 (FIG. 4), the port projections 324 and 326 may extend substantially parallel to a gravitational force direction G. The port projections 324 and 326 may permit the flow channel within the biosensor cartridge 300 to be shaped in a predetermined configuration to facilitate controlling a flow the fluid therein.

Also shown, the microdevice 302 may also include an array 336 of electrical mating contacts 338, which may also be referred to as device contacts or cartridge contacts. The mating contacts 338 may be located on the side surface 332 such that the fluidic access and electrical access to the microdevice 302 are provided on opposite sides of the device body 316 in the illustrated embodiment. The array 336 may be configured to engage an array of electrical contacts of the workstation 200 to communicate with the workstation 200. In the illustrated embodiment, the cartridge contacts 338 are contact pads that interface with the electrical contacts of the workstation 200. The contact pads may be substantially flush with a surface of the device side surface 332 to allow the microdevice 302 to slidably engage the workstation 200. However, in alternative embodiments, the cartridge contacts 338 may be located within sockets or may have beams or tails that project away from the device side surface 332. Furthermore, the cartridge contacts 338 may be pogo pins.

To assemble the biosensor cartridge 300, the microdevice 302 may first be constructed by mounting the flow cell 334 to the base substrate 335. In the illustrated embodiment, the flow cell 334 includes an activity detector that is communicatively coupled to electrical circuits within the base substrate 335. The flow cell 334 may be mounted using an adhesive that is sufficient to withstand the environment in which the microdevice 302 operates. The microdevice 302 may then be positioned on an interior surface of the shell 306 such that the array 336 of cartridge contacts 338 is accessible through the window 312. The frame 317 may be mounted to the shell 308 so that the microdevice 302 is disposed within the restricted space. Alternatively, the frame 317 may be mounted to the shell 306 or integrally formed with the shell 306.

As shown, when the shells 306 and 308 are coupled together, the inlet and outlet ports 320 and 322 and the engagement area 328 are on a common side surface 314 of the biosensor cartridge 300. The port projections 324 and 326 may extend through the window 310, and the array 336 of cartridge contacts 338 may be accessible through the window 312. Furthermore, the microdevice 302 may be moveable or floatable with respect to the casing 304.

Although the casing 304 is shown as being constructed from separate shells 306 and 308, in alternative embodiments, the housing or casing 304 may be integrally formed with the microdevice 302. For example, the components that comprise the microdevice 302 may also form the housing or casing of the biosensor cartridge. Such an alternative housing or casing may have similar dimensions as the casing 304 described above. Thus, in some embodiments, the terms "biosensor cartridge" and "microdevice" may be used interchangeably.

Returning to FIGS. 5 and 6, the biosensor cartridge 300 may include an identification component 340 to provide identification information of the biosensor cartridge 300. The identification component 340 may facilitate identification, tracking, and sorting of the biosensor cartridge 300. For example, the identification information provided by the identification component 340 may be at least one of an identification number, a date of manufacture, a lot number, and a type of biosensor cartridge. The identification information may also relate to the biological or chemical substances inside the microdevice 302 and identify, for example, a genome of interest of DNA fragments therein. The identification information may also provide one or more protocols that may be executed with the biosensor cartridge 300.

As shown, the identification component 340 may include a label 342 that is affixed to the casing 304. The label 342 may include a visual indicator 344, such as a bar code. A user or system may scan the identification component 340 to determine an alpha-numeric code or some other indicator. The user or system may have access to a table that includes a listing of codes or other indicators. The listing may then associate the scanned code or other indicator with the identification information.

Alternatively or additionally, the identification component 340 may include a transmitting device 346, such as an RFID tag physically associated with the biosensor cartridge 300. The transmitting device 346 may include an integrated circuit for storing and processing information and/or modulating and demodulating a radio-frequency (RF) signal. The transmitting device 346 may also include an antenna for receiving and transmitting the signal. In such embodiments where the transmitting device is an RFID tag, the RFID tag may be one of an active RFID tag that has a battery for transmitting signals autonomously, a passive RFID tags that requires an external source to provoke signal transmission, and a battery assisted passive (BAP) RFID tag that requires an external source to activate the RFID tag.

In some embodiments, the system receptacle 212 and the identification component 340 may automatically establish a communication link between each other. For example, the system receptacle 212 may automatically scan the identification component 340 when the biosensor cartridge 300 is inserted into the system receptacle 212. The system receptacle 212 may also automatically receive the identification information from, for example, the transmitting device 346 when the biosensor cartridge 300 is within a predetermined distance from the workstation 200. The workstation 200 may then communicate information to the user that relates to the biosensor cartridge 300. For example, the workstation 200 may automatically notify the user that the biosensor cartridge 300 has been inserted into the system receptacle 212. The workstation 200 may then display information on the user interface 214 and/or automatically prompt the user to select certain options or features.

Figure 7:
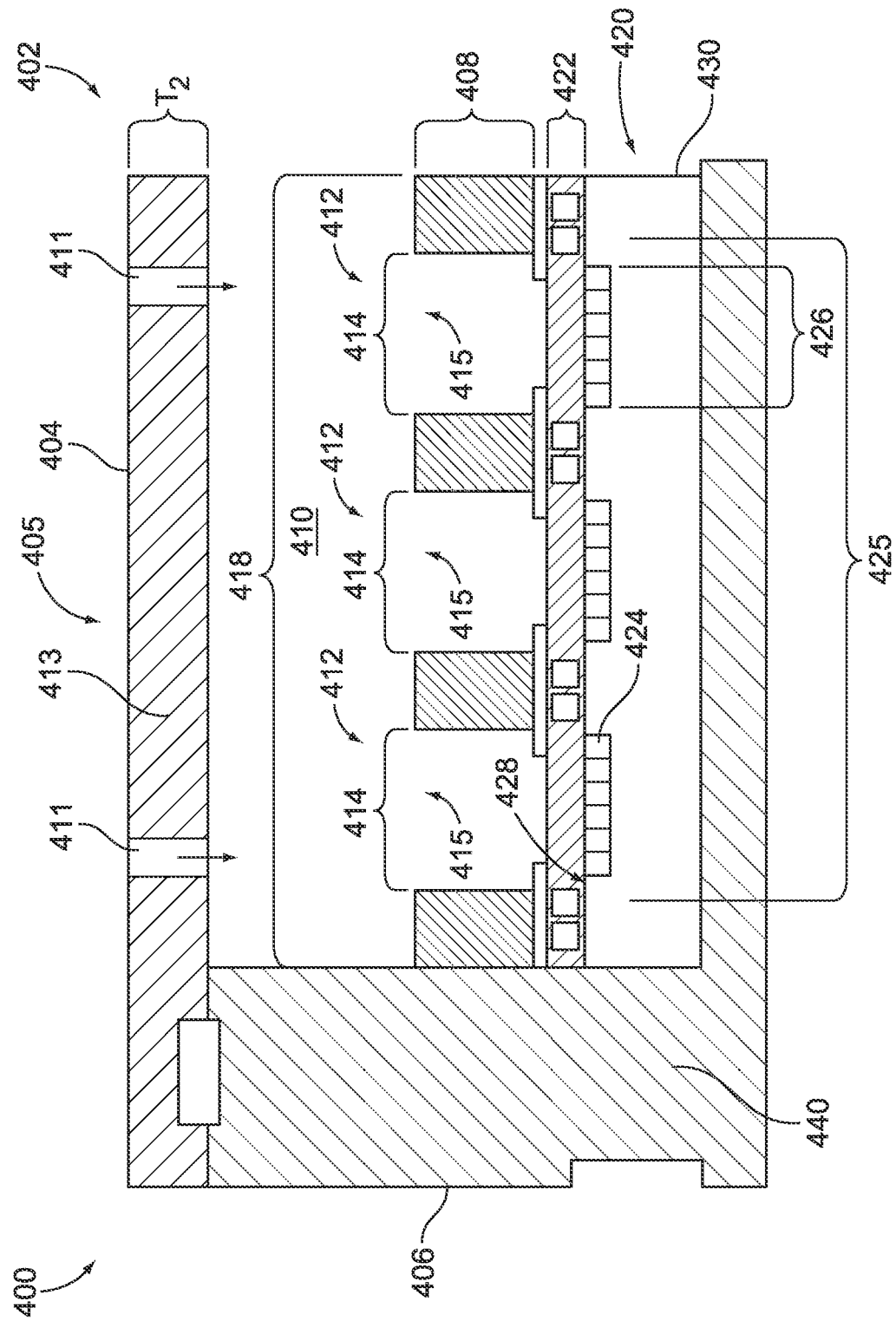
FIG. 7 illustrates a cross-section of a microdevice formed in accordance with one embodiment.

FIG. 7 shows a side view of an exemplary microdevice 400 formed in accordance with one embodiment. The microdevice 400 may be used in or may form a biosensor cartridge, such as the biosensor cartridge 300. As shown, the microdevice 400 may include a flow cell 402 that includes a flow cover 404 mounted to sidewalls 406 (only one sidewall 406 is shown in FIG. 7). The flow cell 402 may also include a reaction substrate or substrate layer 408. The flow cell 402 may define a flow channel 410 between the substrate layer 408 and the flow cover 404. As shown, the flow cover 404 includes two inlet channels 411 that are fluidicly coupled to an inlet port (not shown). Fluid in the flow channel 410 may flow out of the page to one or more outlet channels that are fluidically coupled to an outlet port (not shown).

In some embodiments, the flow cover 404 has an exterior surface 405 that forms an engagement area that is sized and shaped to interface with a thermal element (not shown) of a thermocycler. The flow cover 404 may comprise a thermally conductive material that extends along the flow channel 410. The flow cover 404 may form a cover wall 413 having a uniform thickness $T_2$ in portion(s) that extend along the flow channel 410. As such, thermal energy may more evenly transfer between a thermal element and the fluid within the flow channel 410. In some embodiments, the flow cover 404 comprises a non-transparent material. Optionally, the material may be transparent in alternative embodiments. The flow cover 404 may be attached to the sidewalls 406 using one or more attachment mechanisms. For example, the flow cover 404 may be attached through an interference fit or by using an adhesive or fastener.

The substrate layer 408 comprises a substrate material that facilitates conducting desired reactions. As shown, the substrate layer 408 includes a substrate field 418 that includes a plurality of reaction sites 412 where desired reactions may occur. In the illustrated embodiment, the reaction sites 412 are reaction chambers 414 that each defines a separate spatial region or volume. The reaction chambers 414 may include apertures 415 that open to the flow channel 410 so that the corresponding reaction chambers 414 are in fluid communication with the flow channel 410. The reaction chambers 414 may be sized and shaped for a desired purpose. For example, the reaction chambers 414 may be sized and shaped to accommodate a single DNA capture bead, such as those used in known pyrosequencing protocols. In addition to the DNA bead, the reaction chambers 414 may hold smaller packing beads and/or beads having reagents and enzymes immobilized thereon.

However, in alternative embodiments, the reaction sites are not required to be spatially or physically separated from each other. For example, reaction sites may be located on a planar surface in a predetermined manner (e.g., rows and columns of reactions sites) where each reaction site comprises a portion of the planar surface. Examples of such arrangements may be found on a microarray. In other embodiments, reaction sites may be located on a surface of an elongated channel. The reaction sites may include randomly located clusters or colonies of biomolecules that are immobilized on the surface. As such, the reaction sites may be areas along a surface in addition to spatial regions defined by reaction chambers.

The microdevice 400 may also include an activity detector 420 that is coupled to the flow cell 402. The activity detector 420 is configured to detect activity that is indicative of one or more desired reactions occurring within the microdevice 400. The activity detector 420 includes an array 425 of pixels 424 that are configured to detect activity indicative of a desired reaction from within or along the substrate layer 408. In some embodiments, a pixel area of each pixel 424 is less than about 50 microns. In more particular embodiments, the pixel area is less than about 10 microns. An average read noise of each pixel 424 may be, for example, less than about 150 electrons. In more particular embodiments, the read noise may be less than about 5 electrons. The resolution of the array 425 may be greater than about 0.5 Mpixels. In more specific embodiments, the resolution of the array 425 may be greater than about 5 Mpixels and, more particularly, greater than about 10 Mpixels.

The array 425 of pixels 424 may have a fixed position relative to the substrate field 418. As shown in FIG. 7, the array 425 comprises sub-arrays 426 of pixels 424 in which the sub-arrays 426 are configured to detect activity from a corresponding one reaction chamber 414. In the illustrated embodiment, the activity detector 420 is affixed to the substrate layer 408. Optionally, the activity detector 420 and the substrate layer 408 may be attached to each other through an intermediate layer 422. The intermediate layer 422 may comprise a material or have features that permit the pixels 424 to detect the activity indicative of the desired reaction.

In the illustrated embodiment, the activity detector 420 includes a microcircuit arrangement, such as the microcircuit arrangement described in U.S. Pat. No. 7,595,883, which is incorporated herein by reference in the entirety. More specifically, the activity detector 420 may comprise an integrated circuit having a planar array of photodetectors (i.e., the pixels 424) arranged on a side 428 of a detector substrate 430. The photodetectors may be configured to detect light signals that are emitted from within the reaction chambers 414. The side 428 may interface with the substrate layer 408. Circuitry formed within the detector substrate 430 may be configured for at least one of signal amplification, digitization, storage, and processing. The circuitry may collect and analyze the detected activity and generate signals for communicating detection data to a bioassay system. The signals may be transmitted through electrical contacts of the microdevice 400 or a biosensor cartridge, such as the cartridge contacts 338 (FIG. 6). The circuitry may also perform additional analog and/or digital signal processing. As such, the array 425 of pixels 424 may be communicatively coupled to the electrical contacts that interface with a bioassay system. Furthermore, the circuitry may also include an identification component or module that is configured to provide identification information to the bioassay system.

Figure 8:
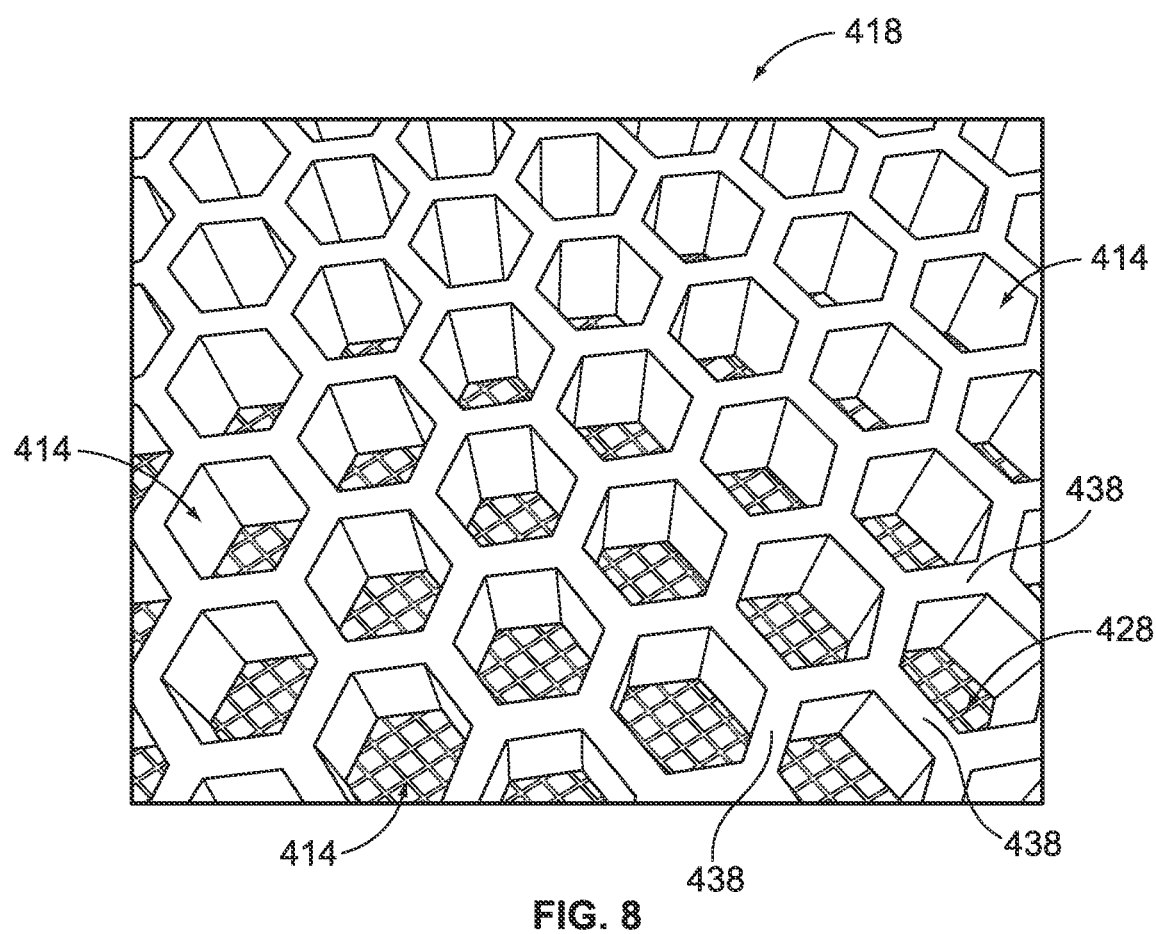
FIG. 8 illustrates a perspective view of a portion of the microdevice shown in FIG. 7.
Figure 9:
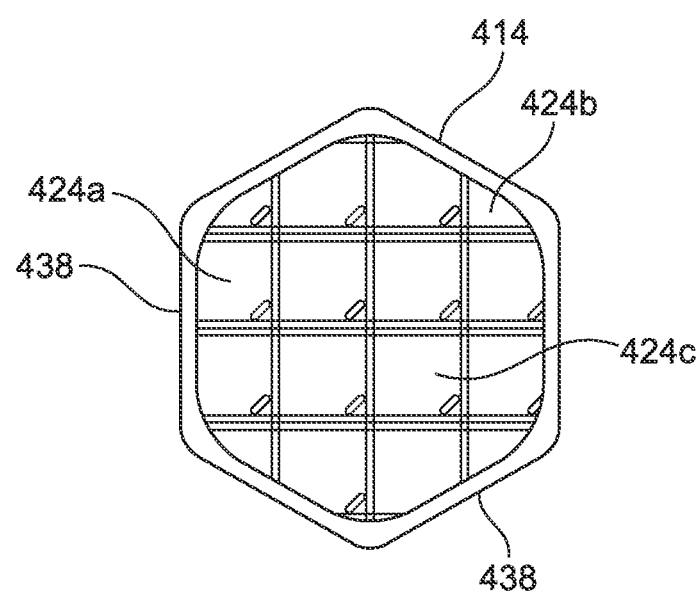
FIG. 9 is a plan view of a reaction chamber that may be used with the microdevice of FIG. 7.
Figure 10:
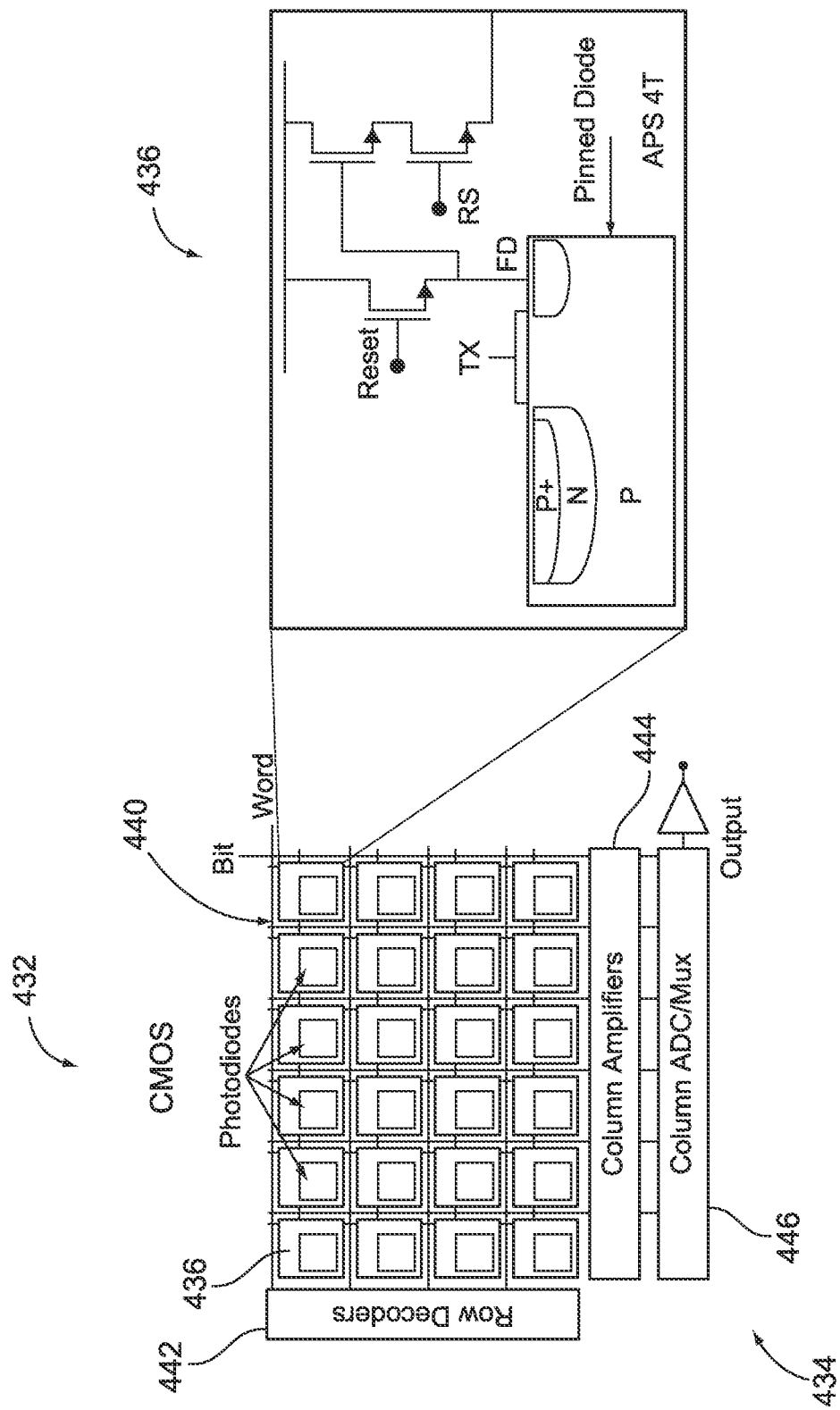
FIG. 10 is a schematic illustration of an exemplary activity detector formed in accordance with various embodiments.

FIGS. 8-10 illustrate exemplary activity detectors in greater detail. FIG. 8 is a perspective view of a portion of the substrate field 418. At least a portion of the intermediate layer 422 (FIG. 7) may include wire-bonding for attaching the substrate layer 408 (FIG. 7) to the side 428 of the activity detector 420. The substrate layer 408 may be deposited onto the wire-bonding of the intermediate layer 422. The substrate layer 408 may comprise a polymer material, such as SUB. In the illustrated embodiment, the reaction chambers 414 have a predetermined pattern along the substrate layer 408 (i.e., the reaction chambers 414 form an array). For example, as shown in FIG. 8, the reaction chambers 414 may have a regular hexagonal-shape cross-section and form a honeycomb-like lattice along the substrate layer 408. Each reaction chamber 414 may be separated from adjacent reaction chambers 414 by chamber walls 438. In the illustrated embodiment, the chamber walls 438 have a common thickness. Optionally, interior surfaces of the chamber walls 438 may be hydrophilic or hydrophobic. Furthermore, an exterior surface of the chamber walls 438 that faces away from the activity detector 420 may partially define the flow channel 410. The exterior surface may extend along a plane to facilitate providing a desired flow of fluid through the flow channel 410 (FIG. 7). The exterior surface may also be hydrophilic or hydrophobic.

FIG. 9 is a plan view of a single reaction chamber 414 and the pixels 424 within the reaction chamber 414. In some embodiments, the substrate layer 408 (FIG. 7) has a fixed position relative to the activity detector 420 so that the reaction chambers 414 have known spatial locations relative to at least one predetermined pixel 424. The at least one predetermined pixel 424 detects activity of the desired reactions from the reaction chamber 414. As such, the reaction chambers 414 may be assigned to at least one pixel 424. To this end, the circuitry of the activity detector 420 may include kernels that automatically associate detection signals provided by predetermined pixels 424 with the assigned reaction chambers 414. By way of example, when detection signals are generated by pixels 424 shown in FIG. 9, the detection signals will automatically be associated with the reaction chamber 414 shown in FIG. 9. Such a configuration may facilitate processing and analyzing the detection data. For instance, the detection signals from one reaction chamber may automatically be located at a certain position on an image.

Also shown in FIG. 9, in some embodiments, a detection surface of the pixels 424 is at least partially covered or obstructed such that the covered detection surface is unable to detect activity. More specifically, the reaction chamber 414 has a plurality of pixels 424, including partially covered pixels 424A and 424B and an entirely exposed pixel 424C. The pixels 424A and 424B are partially covered by the chamber walls 438 of the reaction chamber 414. In some embodiments, kernels of the circuitry of the activity detector 420 may modify values of the detected activity to provide a better representation of the detected activity within the reaction chamber 414. For example, the circuitry may include a kernel for weighting the values of the activity detected by the pixels 424A and 424B.

FIG. 10 provides a schematic illustration of an exemplary activity detector 432 that may be used in various embodiments described herein. For example, the activity detector 432 may be used as the activity detector 420 shown in FIG. 7. The activity detector 432 may be manufactured as a single chip through a CMOS-based fabrication processes. As shown, the activity detector 432 includes a two-dimensional array 440 of photodiodes or pixels 436 that are communicatively coupled to circuitry 434. The array 440 is communicatively coupled to a row decoder 442 and a column amplifier or decoder 444. The column amplifier 444 is also communicatively coupled to a column analog-to-digital converter (Column ADC/Mux) 446. Other circuitry may be coupled to the above components, including a digital signal processor and memory.

FIG. 10 also includes a schematic illustration of a photodiode 436. In some embodiments, the photodiode 436 may be configured to detect a predetermined wavelength of light that is indicative of the desired reactions. As shown, the photodiode 436 may include a P-type substrate having an N-type doping region.

Figure 11:
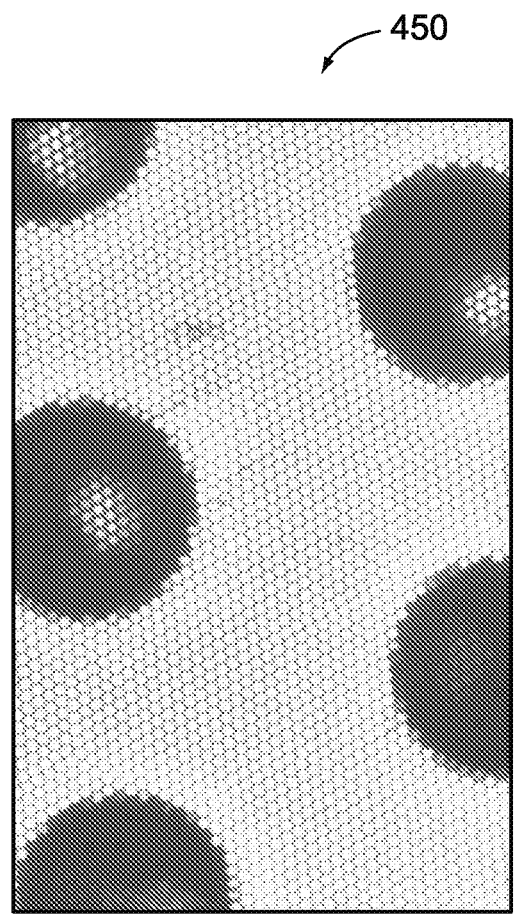
FIG. 11 is an image of a fiber-optic faceplate that may be used in various embodiments.
Figure 12:
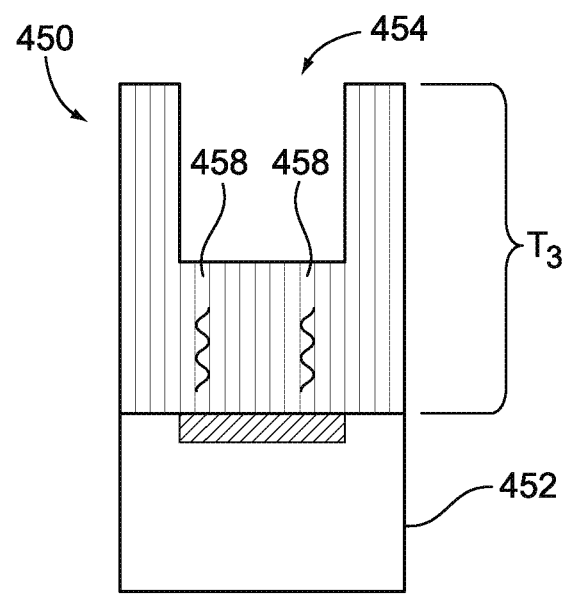
FIG. 12 is a cross-section of the faceplate shown in FIG. 11.

FIGS. 11 and 12 illustrate a fiber-optic faceplate 450 that may be used as the substrate layer 408 (FIG. 7) in alternative embodiments. FIG. 11 is an image showing a plan view of the faceplate 450, and FIG. 12 is a cross-section of the faceplate 450 that is interfacing with an activity detector 452. As shown in FIG. 12, the activity detector 452 may be similar to the activity detector 420 (FIG. 7) or, in a more particular embodiment, the activity detector 436 (FIG. 10). The faceplate 450 may be manufactured from a fiber-optic bundle comprising a plurality of optical fibers of a polymer material (e.g., SU8) that are fused together and cut to form a substrate layer or plate having a thickness $T_3$. The faceplate 450 may be subsequently etched or machined to form a plurality of reaction chambers 454. The reaction chamber 454 may have similar dimensions and functions as the reaction chamber 414 (FIG. 7) described above. As shown, optical fibers 458 below the reaction chamber 454 may transmit light signals that are emitted from within the reaction chamber 454 to a pixel 456 of the activity detector 452. In some embodiments, circuitry of the activity detector 452 may assign at least one pixel 456 to the reaction chamber 454 to facilitate subsequent processing or analysis.

However, the activity detector 420 is not limited to the above constructions or uses as described above. In alternative embodiments, the activity detector may take other forms. For example, the activity detector may comprise a CCD device, such as a CCD camera, that is coupled to a flow cell or is moved to interface with a flow cell having reaction sites therein. In other embodiments, the activity detector may be a CMOS-fabricated sensor, including chemically sensitive field effect transistors (chemFET), ion-sensitive field effect transistors (ISFET), and/or metal oxide semiconductor field effect transistors (MOSFET). Such embodiments may include an array of field effect transistors (FET's) that may be configured to detect a change in electrical properties within the reaction chambers. For example, the FET's may detect at least one of a presence and concentration change of various analytes. By way of example, the array of FET's may monitor changes in hydrogen ion concentration. Such activity detectors are described in greater detail is U.S. Patent Application Publication No. 2009/0127589, which is incorporated by reference in the entirety for the use of understanding such FET arrays.

FIGS. 13-22 illustrate different flow covers that may be used in various embodiments, such as in the biosensor cartridge 300 (FIG. 5) or microdevice 400 (FIG. 7). Each of the flow covers in FIGS. 13-22 include inlet and outlet ports configured to fluidicly couple the corresponding flow cover (or flow cell) to a fluid network. Embodiments described herein may facilitate providing a desired flow of fluid across one or more reaction sites. For example, embodiments described herein may facilitate providing a uniform flow of fluid across the reaction sites. In some embodiments, flow cells may include a flow cover that is integrally formed with a substrate layer. In other embodiments, the flow cover may be coupled or mounted to the substrate layer. FIGS. 13-22 illustrate such flow covers. Furthermore, it is understood that the various features described below with respect to the flow covers may also be incorporated into flow cells.

Figure 13:
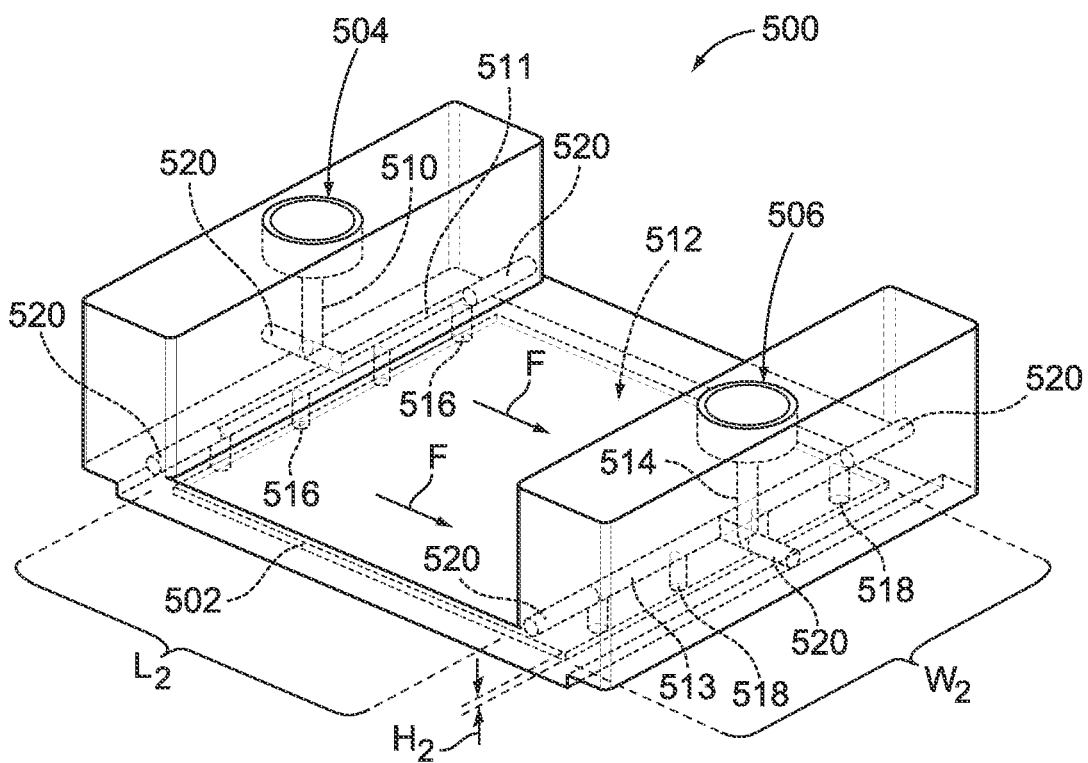
FIG. 13 is a top perspective view of a flow cover that may be used in various embodiments.
Figure 14:
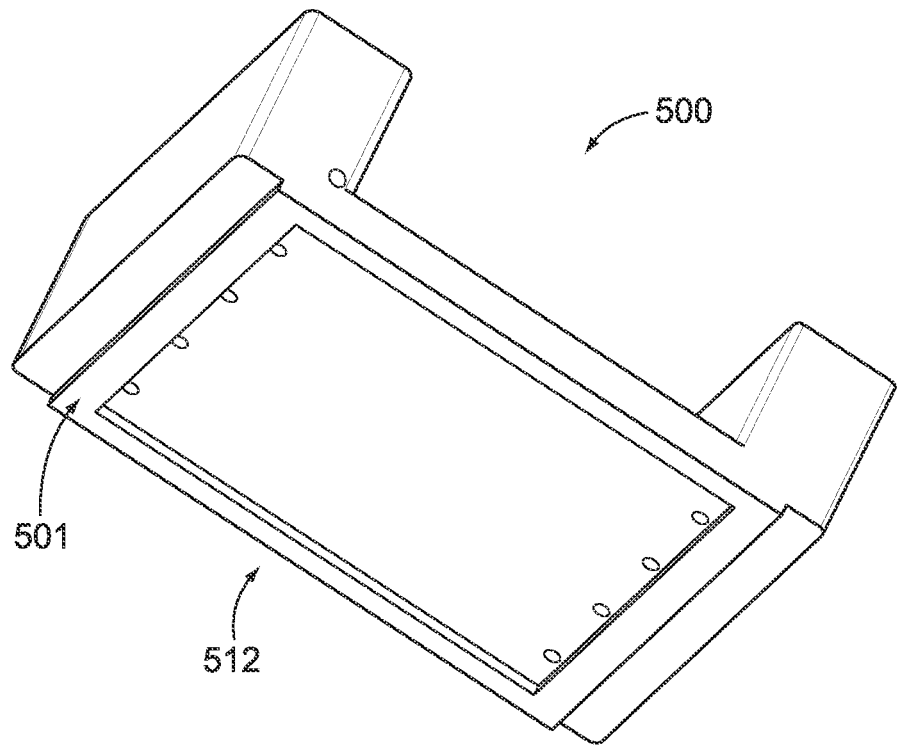
FIG. 14 is a bottom perspective view of the flow cover of FIG. 13.

FIG. 13 is a top perspective view of a flow cover 500 illustrating a flow channel 502 in phantom, and FIG. 14 is a bottom perspective view of the flow cover 500. The flow cover 500 may have a mounting surface 501 (FIG. 14) that is configured to be mounted to another element or component to form a biosensor cartridge or microdevice. For example, the flow cover 500 may be mounted to a substrate layer or some other base.

As shown in FIG. 13, the flow channel 502 extends between inlet and outlet ports 504 and 506 and defines a volume in which fluid may flow therebetween. As shown, the flow channel 502 includes an input region 510 that receives fluid through the inlet port 504, a diffuser region 511 that includes one or more inlet channels 516, a field region 512 that is configured to direct the fluid across a substrate field (not shown) that includes one or more reaction sites, a collector region 513 that receives the fluid from the field region 512, and an output region 514 that delivers the fluid to the outlet port 506. Each of the channel regions 510-514 of the flow channel 502 may be sized and shaped with respect to each other to provide a desired flow of fluid across the substrate field.

As shown, the field region 512 of the flow channel 502 may have a length $L_2$ that extends along a direction of the flow of the fluid (indicated by the arrows F), a width $W_2$ that extends perpendicular to the length $L_2$, and a height $H_2$. The mounting surface 501 (FIG. 14) may form a perimeter of the field region 512. In the flow cover 500, the field region 512 may be substantially rectangular. For example, each dimension (i.e., the length $L_2$, width $W_2$, and height $H_2$) may be substantially uniform throughout the field region 512. However, in alternative embodiments, the field region 512 may have different shapes and dimensions. Furthermore, each dimension may change as said dimension extends lengthwise or widthwise.

Fluid may enter through the inlet port 504 and into the input region 510. The diffuser region 511 receives the fluid and separates the volume to a plurality of inlet channels 516. The inlet channels 516 deliver the fluid to the field region 512. As shown, the inlet channels 516 may be distributed across the width $W_2$ of the field region 512. The fluid flows across the substrate field (not shown) and is removed by outlet channels 518 of the collector region 513. The fluid is then removed from the flow cover 500 through the output region 514.

In some embodiments, the input and output regions 510 and 514 extend in a direction that is perpendicular to the field region 512. More specifically, in operation the fluid may flow through the input and output regions 510 and 514 in a direction that is parallel to a gravitational force direction G and perpendicular to a flow direction of the field region 512 (i.e., a general direction in which the fluid flows through the field region 512). Moreover, the fluid may flow through the input and output regions 510 and 514 in a direction that is perpendicular to a flow direction through the diffuser and collector regions 511 and 513.

The flow cover 500 may be integrally formed, for example, by an injection molding process. More specifically, rods or columns may extend through a void of a molding apparatus where the regions 510, 511, 513, and 514 are to be located. A block may extend into the void as well to form the field region 512. After a resin is injected into the void of the molding apparatus, the rods and block may be removed thereby leaving cavities that are used to form the channel regions 510-514. Plugging elements 520 may then be formed or inserted into the various cavities to define the various channel regions 510-514.

Figure 15:
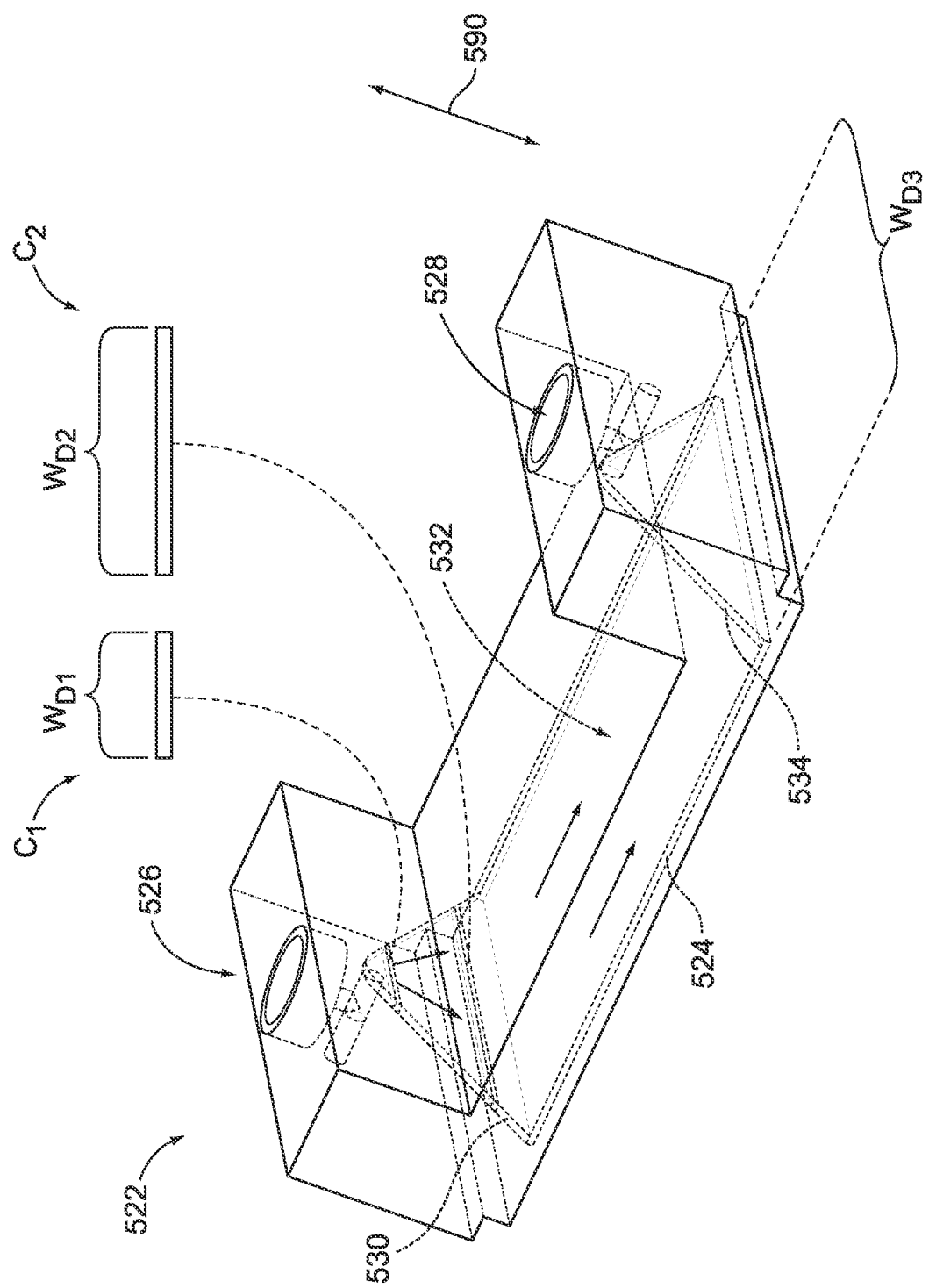
FIG. 15 is a top perspective view of another flow cover that may be used in various embodiments.

FIG. 15 is a top perspective view of a flow cover 522 illustrating a flow channel 524 in phantom. As shown, the flow channel 524 extends between inlet and outlet ports 526 and 528 and includes a plurality of channel regions, including a diffuser region 530, a field region 532, and a collector region 534. The diffuser region 530 is shaped to distribute the fluid to the field region 532 and may be oriented such that the flow direction is parallel to a vertical axis 590. The diffuser region 530 has first and second flow cross-sections $C_1$ and $C_2$ that are taken perpendicular to the vertical axis 590. The term "flow cross-section," as used herein, is a cross-section of a fluidic channel that is taken substantially transverse to a direction of the flow of fluid. For example, the flow of fluid through flow cross-sections $C_1$ and $C_2$ in FIG. 15 is generally out of (or into) the page.

As shown, the flow cross-section $C_1$ is located closer to the inlet port 526, and the flow cross-section $C_2$ is located closer to the field region 532. In the illustrated embodiment, at least one cross-sectional dimension increases as the diffuser region 530 extends toward the field region 532. More specifically, a width $W_0$ of the diffuser region 530 increases as the diffuser region 530 extends toward the field region 532. When the diffuser region 530 reaches the field region 532, the diffuser and field regions 530 and 532 may have substantially the same width $W_{D3}$. Also shown, the collector region 534 may be similarly shape as the diffuser region 530.

Figure 16:
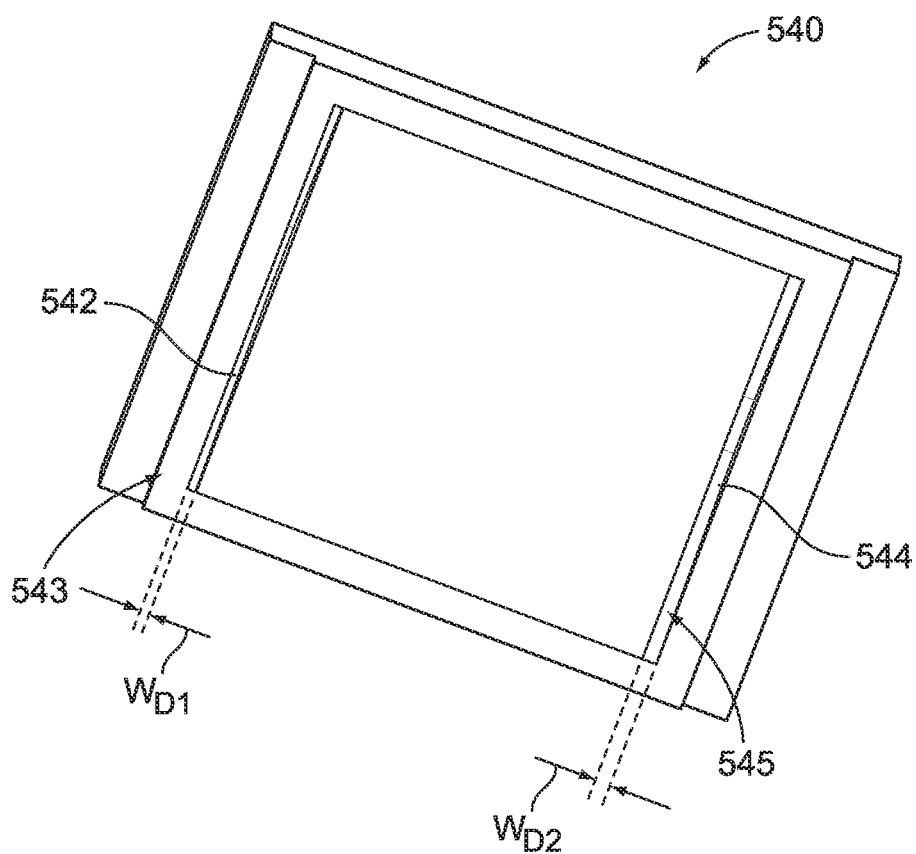
FIG. 16 is a bottom perspective view of another flow cover that may be used in various embodiments.
Figure 17:
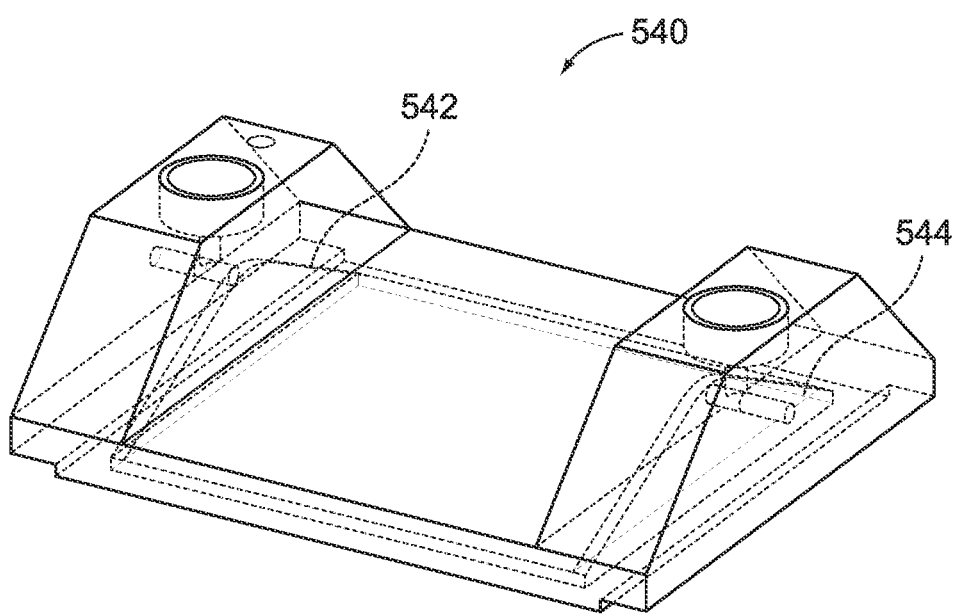
FIG. 17 is a top perspective of the flow cover in FIG. 16.

FIGS. 16 and 17 provide a bottom view and a perspective view, respectively, of a flow cover 540. The flow cover 540 may have similar features as the flow cover 522. However, as shown in FIG. 16, a diffuser region 542 and a collector region 544 may have different dimensions at respective openings 543 and 545. More specifically, the opening 545 of the collector region 544 may have a greater width $W_{O2}$ than a width $W_{O1}$ of the opening 543 of the diffuser region 542.

Figure 18:
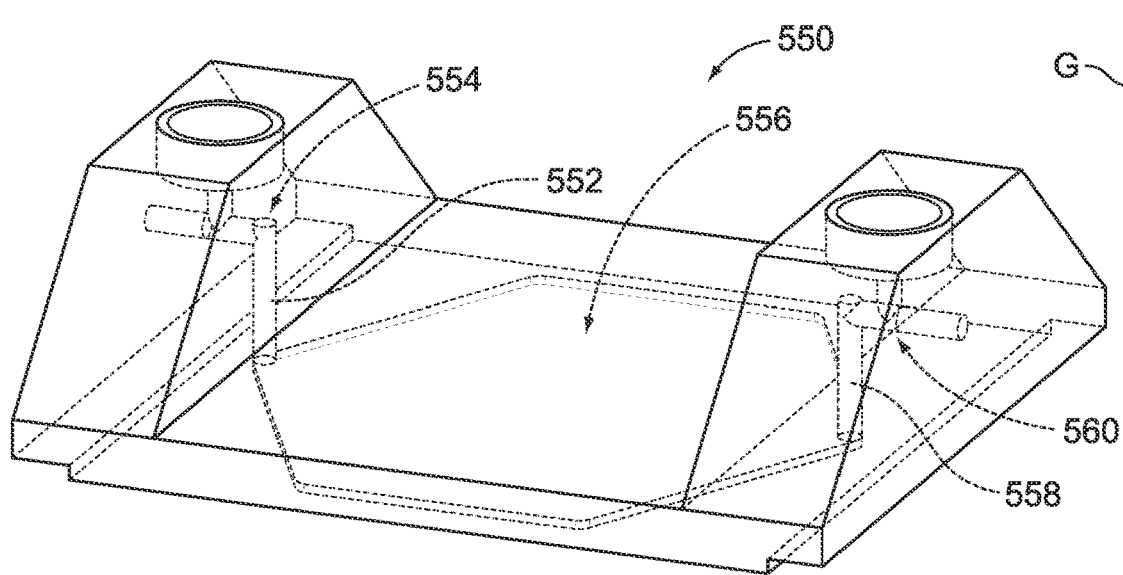
FIG. 18 is a top perspective view of a flow cover formed in accordance with another embodiment.

FIG. 18 is a top perspective view of a flow cover 550. In some embodiments, field regions of the flow channel may be shaped to diffuse (or expand) the flow of fluid or to compress (or contract) the flow of fluid. For example, the flow cover 550 includes an inlet channel 552 of an input region 554 that provides fluid to a field region 556. Fluid may be removed from the field region 556 through an outlet channel 558 of an output region 560. As shown, the field region 556 is oriented in a substantially horizontal manner relative to a gravitational force direction G. The field region 556 may be diamond-shaped such that the flow channel has an increasing cross-section as the fluid initially flows away from the inlet channel 552. The field region 556 may have a uniform cross-section for a middle portion of the field region 556 as the fluid flows therethrough, and then begin to decrease when the fluid is proximate to the outlet channel 558. As such, the flow covers described herein may have horizontal diffuser regions and vertical diffuser regions as well as horizontal collector regions and vertical collector regions.

Figure 19:
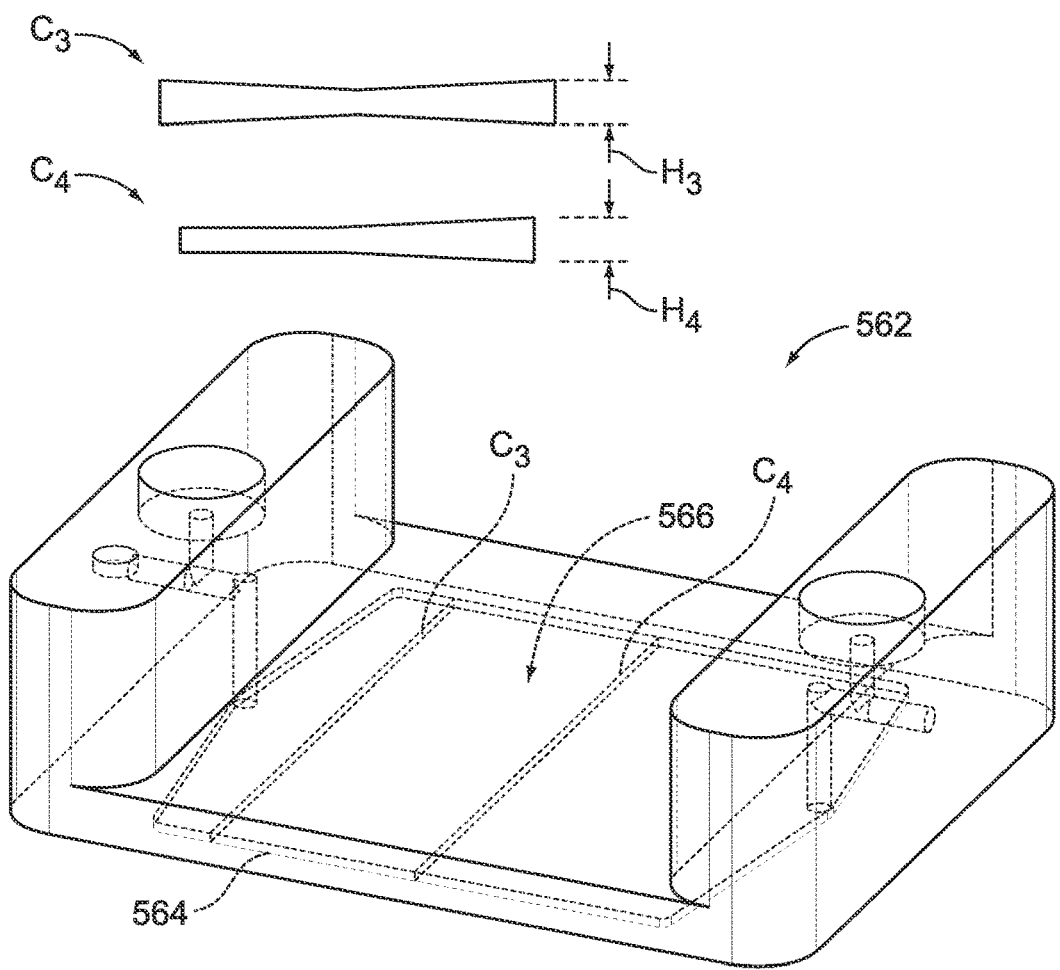
FIG. 19 is a top perspective view of a flow cover formed in accordance with another embodiment.

FIG. 19 is a top perspective view of a flow cover 562. In previously described embodiments, a flow cross-section taken perpendicular to the flow of the fluid may have a height that remained substantially equal to other cross-sections. However, the flow cover 562 includes a flow channel 564 where a height in cross-sections taken perpendicular to the flow of fluid changes. As shown in flow cross-section $C_3$, a height $H_3$ of the cross-section varies therealong. Furthermore, dimensions of the flow cross-section $C_4$ may also be different from the dimensions of the flow cross-section $C_3$. For example, the height $H_4$ may be greater than the height $H_3$. Accordingly, embodiments of flow covers and flow cells described herein may have flow channels and, more specifically, field regions of the flow channels with varying three-dimensional shapes to control a flow of fluid as desired.

Figure 20:
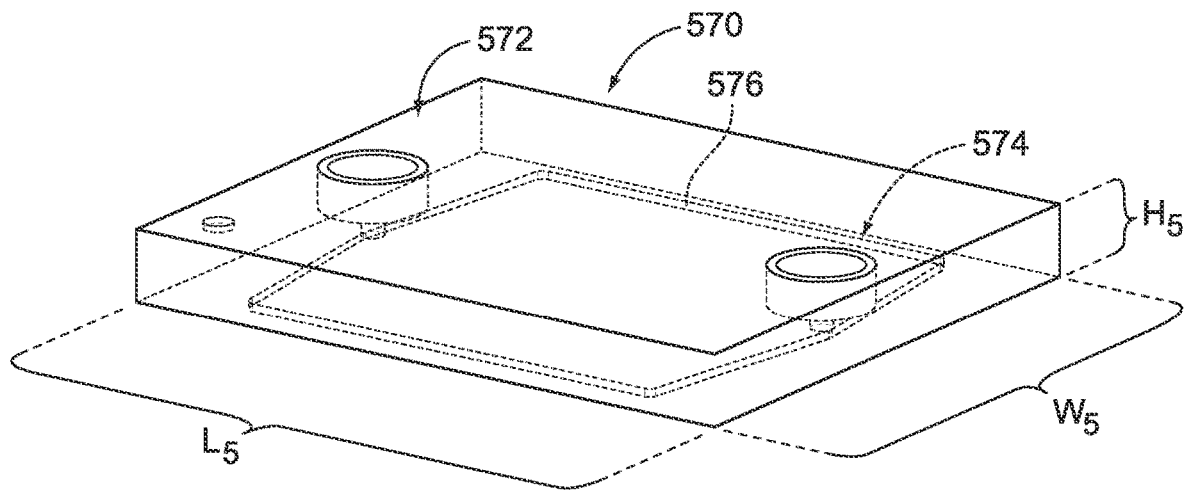
FIG. 20 illustrates an exemplary embodiment of a planar flow cover formed in accordance with various embodiments.

FIG. 20 illustrates an exemplary embodiment of a planar flow cover 570. The flow cover 570 may have a substantially rectangular or block shape and include a height $H_5$, a width $W_5$, and a length $L_5$ that are substantially uniform. As shown, the flow cover 570 may have inlet and outlet ports 572 and 574 that are directly adjacent to a field region 576. As such, fluid entering through the inlet port 572 may immediately enter the field region 576, and fluid exiting the field region 576 may immediately exit the flow cover 570 through the outlet port 574. In the illustrated embodiment, the field region 576 may have similar dimensions as the field region 564. However, in alternative embodiments, the field region 576 may have other dimensions.

Figure 21:
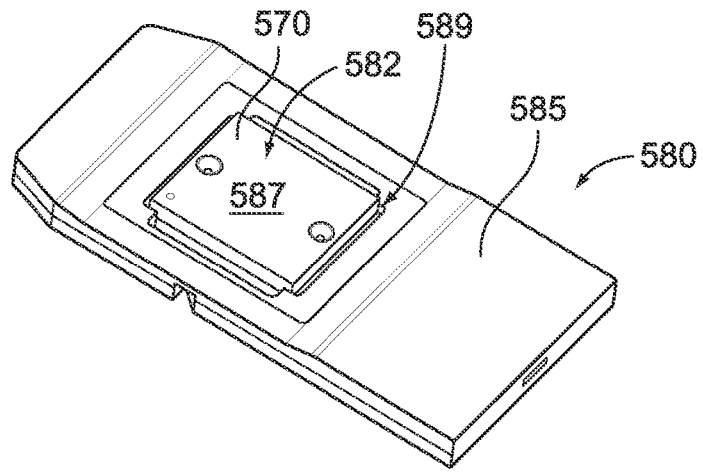
FIG. 21 is a top view of a biosensor cartridge formed in accordance with one embodiment including the flow cover of FIG. 20.
Figure 22:
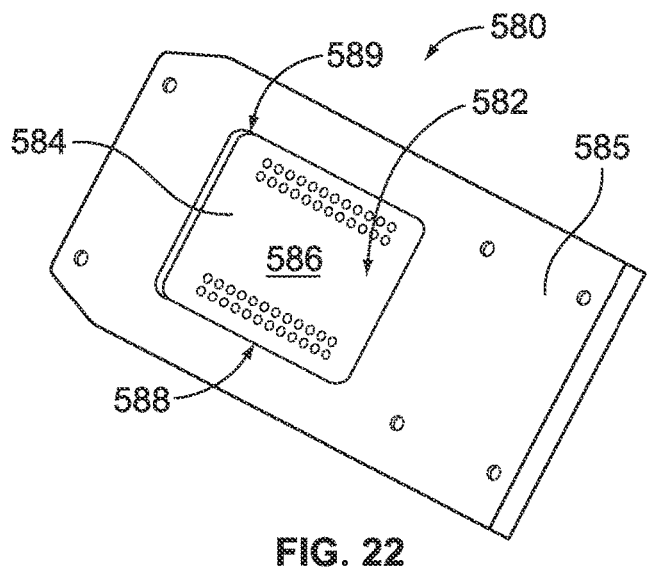
FIG. 22 is a bottom view of the biosensor cartridge of FIG. 21.

FIGS. 21 and 22 are top and bottom views of a biosensor cartridge 580 having a microdevice 582 that comprises the flow cover 570 (FIG. 21) mounted to a base substrate 584 (FIG. 22). As shown, the base substrate 584 includes an exterior side surface 586 having an array of electrical contacts 588 thereon. The microdevice 582 may be held by a housing 585. More specifically, the microdevice 582 may be confined within a restricted space defined by the housing 585. A cavity 589 of the housing 585 may hold the microdevice 582 such that the side surface 586 and an opposite side surface 587 do not clear a surface of the housing 585. In such embodiments, the biosensor cartridge 580 may be inserted into a system receptacle (not shown) without the microdevice 582 snagging or catching a portion of the system receptacle.

Figure 23:
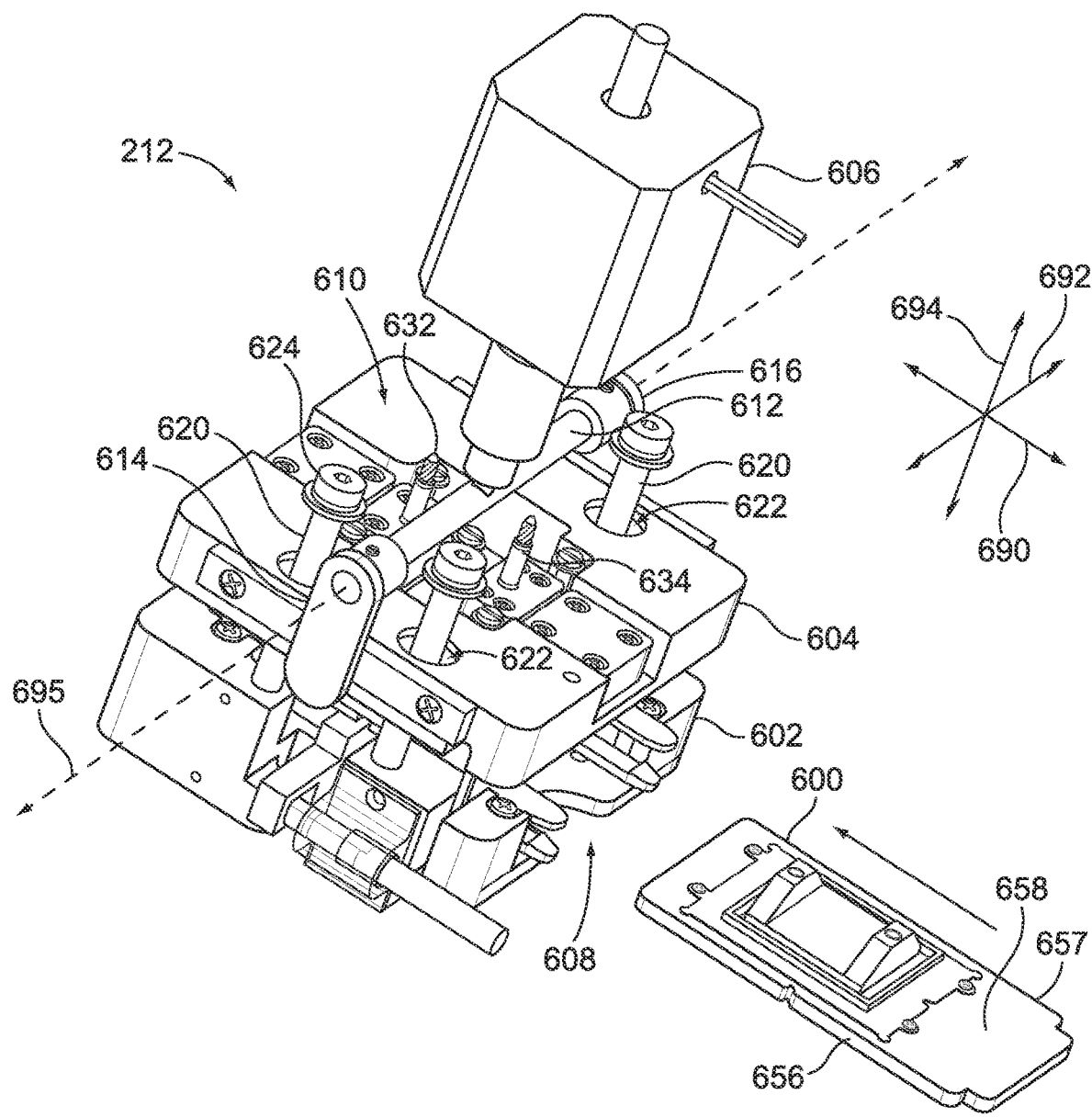
FIG. 23 is a perspective view of a system receptacle formed in accordance with one embodiment.

FIGS. 23-27 illustrate the system receptacle 212 in greater detail. FIG. 23 is a perspective view of the system receptacle 212 before a biosensor cartridge 600 is inserted into the system receptacle 212. The biosensor cartridge 600 may have similar features as described elsewhere, such as with respect to the biosensor cartridges 300 and 580; with respect to the microdevices 102, 235, 302, 400, and 582; with respect to the flow cell 334; and with respect to the flow covers 404, 500, 522, 540, 550, 562, and 570. As shown, the system receptacle 212 is oriented with respect to a longitudinal axis 690, a lateral axis 692, and a vertical axis 694.

As shown in FIG. 23, the system receptacle 212 includes a first receptacle sub-assembly 602, a second receptacle sub-assembly 604, and an actuation device 606 that is operatively coupled to the second receptacle sub-assembly 604. The first and second receptacle sub-assemblies 602 and 604 are vertically stacked with respect to each other and spaced apart in an unengaged position. The system receptacle 212 includes a cartridge slot 608 that may receive the biosensor cartridge 600. The first and second receptacle sub-assemblies 602 and 604 are configured to be moved toward each other into an engaged position. In the engaged position, the biosensor cartridge 600 may be mechanically, electrically, and fluidicly coupled to the workstation 200 (FIG. 3). For example, in the illustrated embodiment, the first receptacle sub-assembly 602 holds the biosensor cartridge 600 in a predetermined position. The actuation device 606 is configured to move the second receptacle sub-assembly 604 in a linear manner along the vertical axis into the engaged position with the first receptacle sub-assembly 602 where the biosensor cartridge 600 may be mechanically, electrically, and fluidicly coupled to the workstation 200.

In the illustrated embodiment, the first receptacle sub-assembly 602 holds the biosensor cartridge 600 in the predetermined position and, as such, is hereinafter referred to as the alignment assembly 602. The second receptacle sub-assembly 604 is moved to engage the alignment assembly 602 and, as such, is hereinafter referred to as the mounting assembly 604. However, in alternative embodiments, the first receptacle sub-assembly 602 may be moved toward the second receptacle sub-assembly 604 or both the first and second receptacle sub-assemblies 602 and 604 may be moved toward each other. Also shown in FIG. 23, a pair of conduits 632 and 634 may be affixed to the mounting assembly 604. The conduits 632 and 634 may be fluidically coupled to the fluid network of the workstation 200.

The actuation device 606 may be coupled to the mounting assembly 604 through a joint assembly 610. The joint assembly 610 is configured to permit the mounting assembly 604 to pivot or shift when moved toward the engaged position so that the mounting assembly 604 may be aligned when engaging the biosensor cartridge 600. In the illustrated embodiment, the joint assembly 610 includes a rod 612 and a pair of rotatable links 614 and 616 that are interconnected by the rod 612. The actuation device 606 may be coupled to the rod 612, and the rotatable links 614 and 616 may be coupled to the mounting assembly 604. The rotatable links 614 and 616 may have inward projections 648 (FIG. 24) that engage the mounting assembly 604. In some embodiments, the inward projections 648 may permit the mounting assembly 604 to shift along an axis that is parallel to the lateral axis 692 and the alignment axis 695. Furthermore, in some embodiments, the inward projections 648 may permit the mounting assembly 604 to rotate along such an axis.

The mounting assembly 604 may also include a plurality of bores 622 that extend through the mounting assembly 604 along the vertical axis 694. The system receptacle 212 may include a plurality of alignment pins 620 that extend through corresponding bores 622. The alignment pins 620 are attached to the alignment assembly 602 at one end and have a stopper 624 at an opposite end. The bores 622 may be shaped relative to the corresponding alignment pins 620 to permit the mounting assembly 604 to pivot or shift when moved toward the engaged position. For example, the bores 622 may have a cross-sectional diameter that is slightly greater than a cross-sectional diameter of the alignment pins 620.

To mount the mounting assembly 604 to the alignment assembly 602 (i.e., move the mounting assembly 604 from the unengaged position to the engaged position), the actuation device 606 may move the mounting assembly 604 in a linear manner toward the alignment assembly 602. As the mounting assembly 604 approaches the alignment assembly 602, the mounting assembly 604 may engage components or portions of the alignment assembly 602 and/or the biosensor cartridge 600. If the mounting assembly 604 is misaligned with the biosensor cartridge 600 and/or the alignment assembly 602, the mounting assembly 604 may at least one of: (a) shift along a plane formed by the longitudinal axis 690 and the lateral axis 692 and (b) pivot about the alignment axis 695 that extends parallel to the lateral axis 692.

Figure 24:
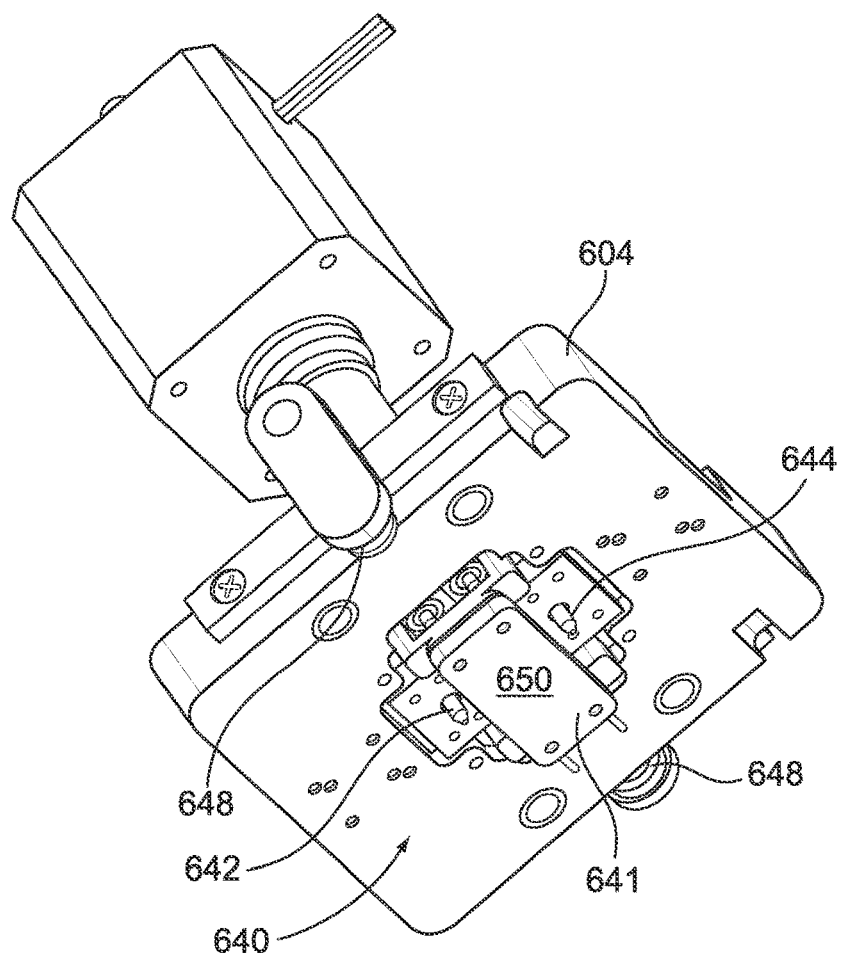
FIG. 24 is a bottom perspective view of a mounting assembly of the system receptacle of FIG. 23.

FIG. 24 is a bottom perspective view of the mounting assembly 604. The mounting assembly 604 may include a mating face 640 that engages the biosensor cartridge 600 (FIG. 23) and the alignment assembly 602 (FIG. 23). As shown, the mating face 640 may include a thermal module or element 641 and nozzles 642 and 644 of the conduits 632 and 634 (FIG. 23). The thermal element 641 includes a surface 650 and is configured to interface with an engagement area of the biosensor cartridge 600 to transfer or absorb heat from the biosensor cartridge. The nozzles 642 and 644 are configured to be inserted into inlet and outlet ports 662 and 664 of the biosensor cartridge 600 to fluidicly couple the workstation 200 (FIG. 3) to the biosensor cartridge 600.

Figure 25:
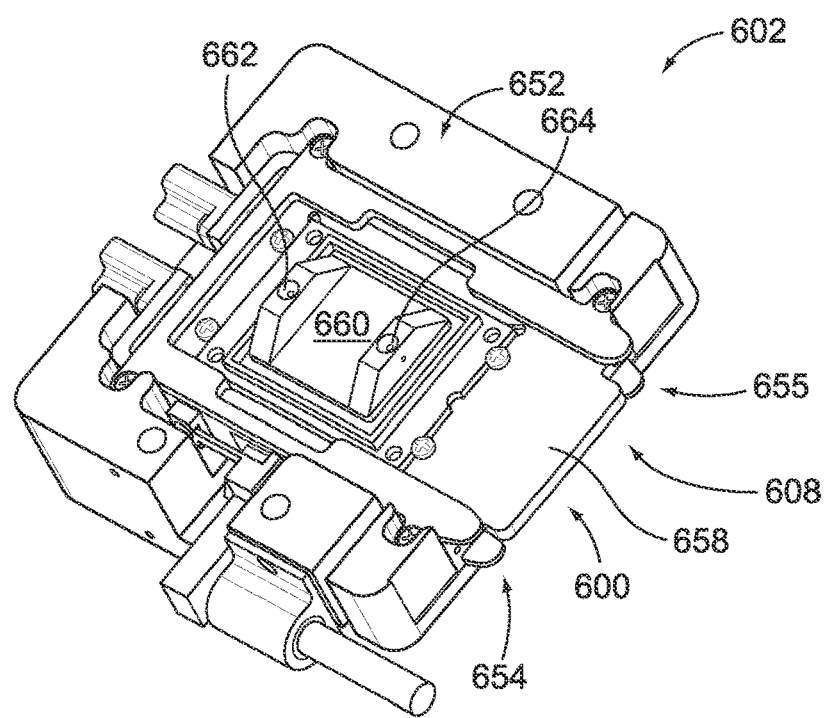
FIG. 25 is a perspective view of an alignment assembly that may be used with the system receptacle of FIG. 23.

FIG. 25 is a perspective view of the alignment assembly 602. The alignment assembly 602 may also include a mating face 652 that engages the mounting assembly 604. The alignment assembly 602 may include tracks or guiderails 654 and 655 that engage opposite edges 656 and 657 (FIG. 24) of a housing or casing 658 of the biosensor cartridge 600. When the biosensor cartridge 600 is inserted into the cartridge slot 608, the guiderails 654 and 655 may direct the biosensor cartridge 600 to a desired slot position as shown in FIG. 25. In the slot position, the biosensor cartridge 600 may be oriented to engage the mating face 640 (FIG. 24) of the mounting assembly 604. More specifically, an engagement area 660 of the biosensor cartridge 600 may face and be positioned to receive the thermal element 641, and inlet and outlet ports 662 and 664 of the biosensor cartridge 600 may open to and be positioned to receive the nozzles 642 and 644.

Figure 26:
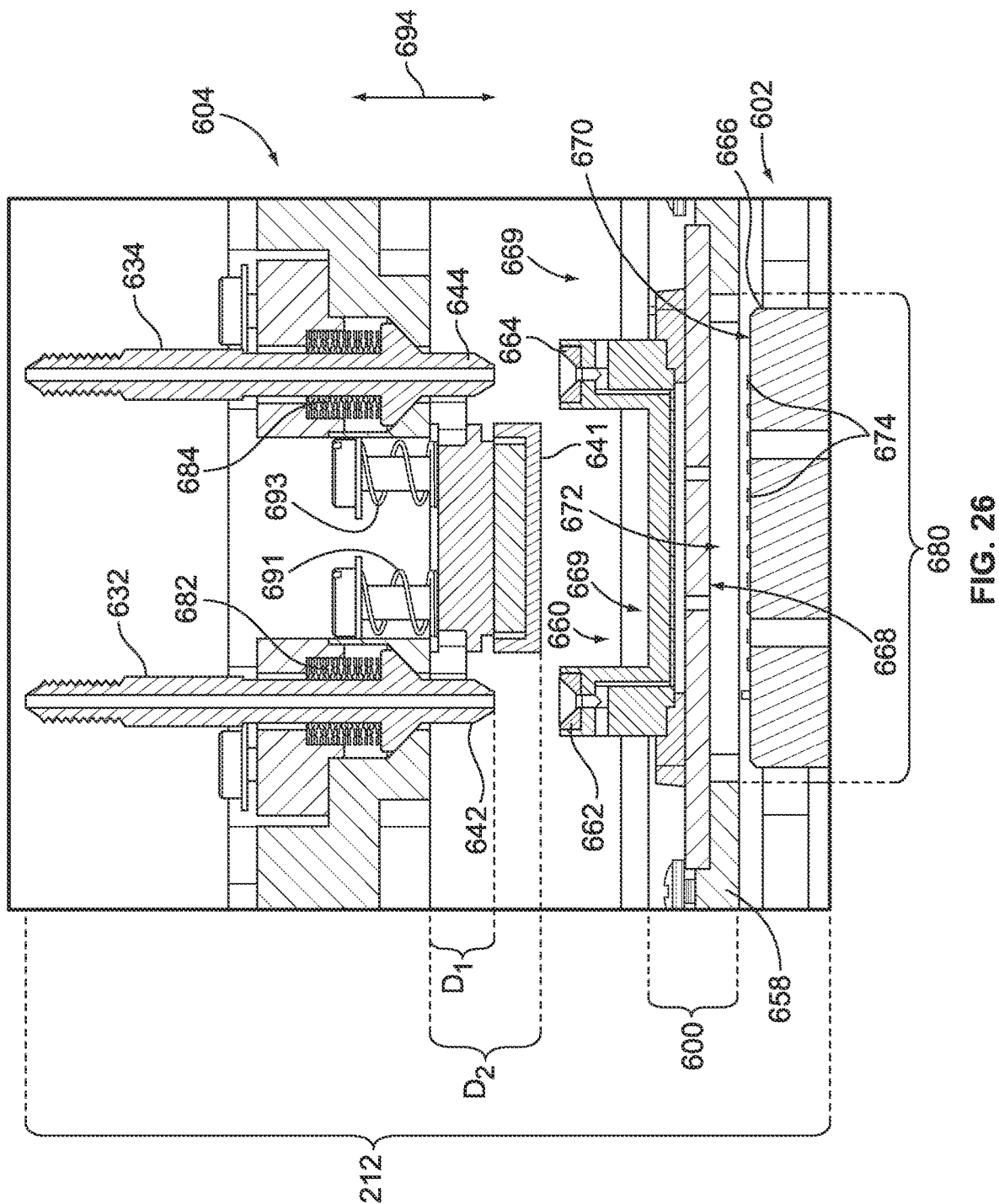
FIG. 26 is a cross-section of the system receptacle in the unengaged position.
Figure 27:
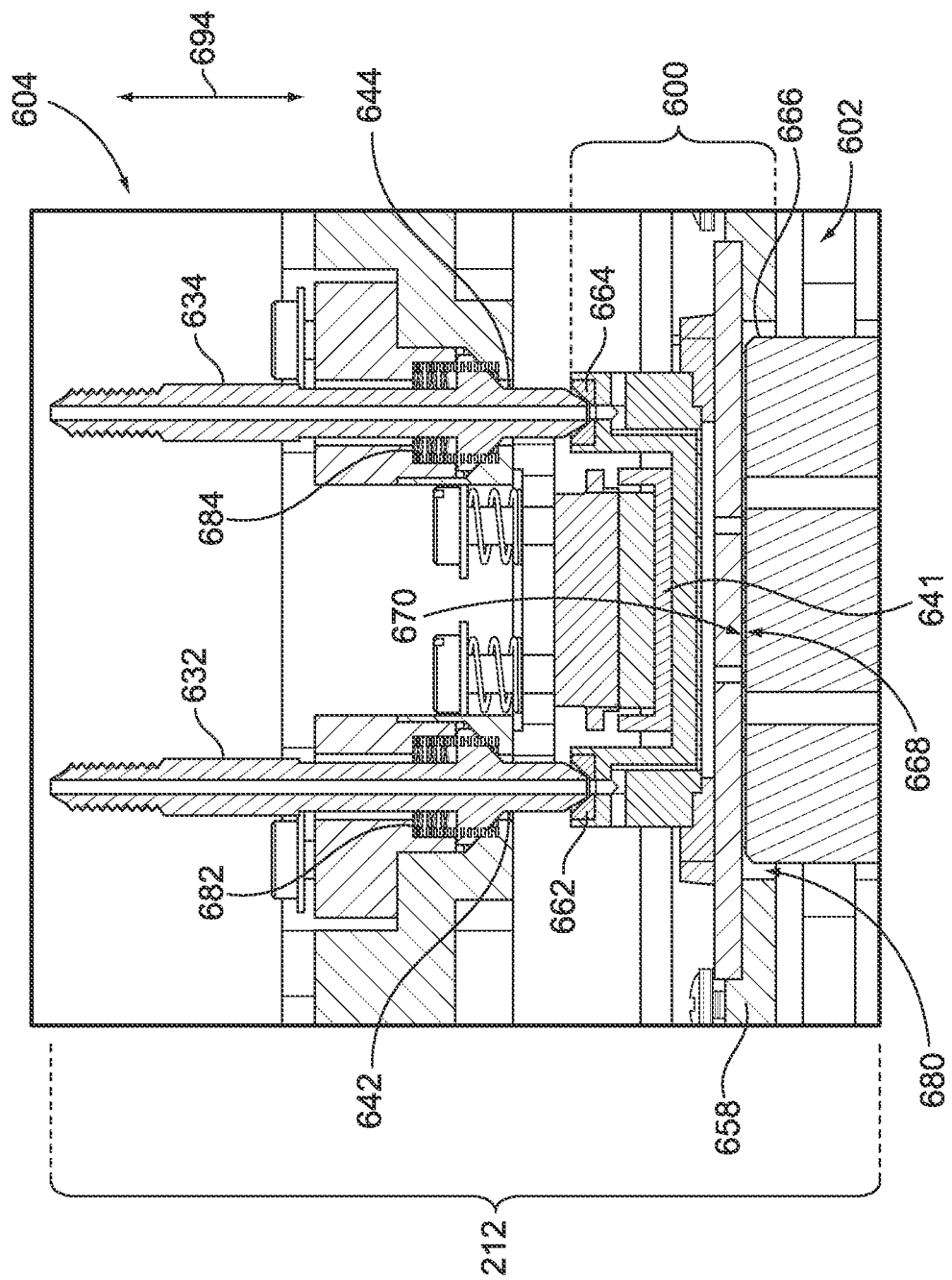
FIG. 27 is a different cross-section of the system receptacle in the engaged position.

FIGS. 26 and 27 are cross-sections of the biosensor cartridge 600 and the system receptacle 212 illustrating the mounting and alignment assemblies 604 and 602 in unengaged and engaged positions, respectively. In both FIGS. 26 and 27, the biosensor cartridge 600 is in the desired slot position. As shown, the system receptacle 212 may also include an electrical connector 666 that electrically engages the biosensor cartridge 600 so that the workstation 200 (FIG. 3) may communicate and/or provide power to the biosensor cartridge 600. For example, the biosensor cartridge 600 may be able to provide detection data regarding any detected activity of desired reactions that occurred in the biosensor cartridge 600. In some embodiments, the electrical connector 666 is located on a first side surface 668 of the biosensor cartridge 600 and the nozzles 642 and 644 and/or the thermal element 641 are located on an opposite second side surface 669 (FIG. 26). The system receptacle 212 may be configured to electrically engage the biosensor cartridge 600 before fluidically engaging the biosensor cartridge 600. Alternatively, the system receptacle 212 may be configured to fluidicly engage the biosensor cartridge 600 before electrically engaging the biosensor cartridge 600. Moreover, the system receptacle 212 may be configured to electrically and fluidicly engage the biosensor cartridge 600 at substantially the same time.

The electrical connector 666 may include a mating side 670 that includes an array 672 of electrical contacts 674 (FIG. 26) (hereinafter referred to as system contacts) that electrically engage electrical contacts (not shown) (hereinafter referred to as cartridge contacts) of the biosensor cartridge 600. In particular embodiments, the system contacts 674 may provide a resilient spring force toward the first side surface 668. For example, the system contacts 674 may include pogo pin contacts or resilient beams that flex to and from the mating side 670 in a direction along the vertical axis 694. Furthermore, the system contacts 674 may include a wipe surface that is sized and shaped to permit some misalignment between one system contact 674 and the corresponding cartridge contact.

In particular embodiments, the electrical connector 666 is moveable to and from the biosensor cartridge 600. For example, the electrical connector 666 may be moved in an axial direction (i.e., along the vertical axis 694) to and from the biosensor cartridge 600. More specifically, the electrical connector 666 may be moveable from an unmated position as shown in FIG. 26, wherein the system contacts 674 are spaced apart from cartridge contacts of the biosensor cartridge 600, to a mated position as shown in FIG. 27, wherein the system contacts 674 and the cartridge contacts are electrically engaged. In some embodiments, the electrical connector 666 is moved through an opening or window 680 of the housing 658 to engage the cartridge contacts.

Also shown in FIGS. 26 and 27, the conduits 632 and 634 (along with the corresponding nozzles 642 and 644) may be separately or independently moveable along the vertical axis 694 to facilitate fluidicly coupling the biosensor cartridge 600 to the fluid network. The mounting assembly 604 may include resilient springs 682 and 684 that reside within respective cavities 686 and 688. The resilient springs 682 and 684 are configured to engage ledges of the conduits 632 and 634 to resist movement in a direction away from the biosensor cartridge 600. As shown in FIG. 26, in the relaxed (i.e., unengaged position), the nozzles 642 and 644 extend a distance $D_1$ away from the mating face 640.

Likewise, the thermal element 641 may be separately or independently moveable along the vertical axis 694 to facilitate maintaining a thermal engagement with respect to the engagement area 660 (FIG. 26) of the biosensor cartridge 600. The mounting assembly 604 may include resilient springs 691 and 693 (FIG. 26) that surround mounting posts that support the thermal element 641. In the relaxed (i.e., unengaged position), the thermal element 641 extends a distance $D_2$ away from the mating face 640. The resilient springs 691 and 693 may resist movement of the thermal element 641 and provide a reactive force that facilitates maintaining the thermal interface between the engagement area 660 and the thermal element 641.

In the illustrated embodiment, after the biosensor cartridge 600 is inserted into the cartridge slot 608 (FIG. 23) and moved to the slot position, the electrical connector 666 may be moved to an engaged position with respect to the first side surface 668 of the biosensor cartridge in which the system contacts 674 electrically engage the cartridge contacts. In such embodiments where the system contacts 674 project from the mating side 670 and provide a resilient spring force toward the first side surface 668, the system contacts 674 may initially engage the cartridge contacts before the electrical connector 666 has been fully moved into the engaged position. If the surfaces of the biosensor cartridge 600 and the electrical connector 666 do not fully engage each other along the interface, the system contacts 674 may facilitate electrically engaging and maintaining the electrical connection throughout operation of the workstation 200. Before the mating face 640 is mounted to the biosensor cartridge 600, in some embodiments, a system controller may notify a user that the electrical connector 666 has properly engaged the biosensor cartridge 600. However, if the electrical connector 666 has improperly engaged the biosensor cartridge 600, the system controller may notify the user that the electrical engagement between the electrical connector 666 and the biosensor cartridge is improper.

As described above, the mating face 640 of the mounting assembly 604 may mount the biosensor cartridge 600 after, before, or at substantially the same time as when the electrical connector 666 has engaged the cartridge contacts. The mating face 640 may be moved toward the biosensor cartridge 600 by the actuation device 606 (FIG. 23). The nozzles 642 and 644 may engage the inlet and outlet ports 662 and 664, respectively, of the biosensor cartridge 600 before the mounting assembly 604 has moved fully into the engaged position. At this time, the nozzles 642 and 644 may be pushed away from the second side surface 669 of the biosensor cartridge 600 (i.e., in a direction opposite to the mounting direction). The resilient springs 682 and 684 may resist the movement. As shown in FIG. 27, stored (or potential) energy of the resilient springs 682 and 684 may facilitate maintaining the fluidic connection between the inlet and outlet ports 662 and 664 and the nozzles 642 and 644 when the mounting assembly 604 is in the fully engaged position with respect to the biosensor cartridge 600 and the alignment assembly 602. For example, the stored energy may maintain the fluidic connection during flow pressure changes of an assay protocol.

Furthermore, the thermal element 641 may press against the engagement area 660 of the biosensor cartridge when the mounting assembly 604 is moved into the engaged position. The resilient springs 691 and 693 may resist movement of the thermal element 641 in a direction opposite to the mounting direction (or away from the biosensor cartridge 600). In the engaged position, stored (or potential) energy of the resilient springs 691 and 693 may facilitate maintaining the thermal engagement between the thermal element and the engagement area 660 of the biosensor cartridge 600.

In some embodiments, the microdevice 628 of the biosensor cartridge 600 may be floatable within the housing 658. Dimensions of the restricted space of the housing 658 that holds the microdevice 628 may be greater than the dimensions of the microdevice. In such embodiments, the microdevice may slide within the housing 658 to facilitate properly aligning the biosensor cartridge 600. For example, if the nozzles 642 and 644 are misaligned with respect to openings of the inlet and outlet ports 662 and 664, the microdevice 628 may slide in a lateral manner into a properly aligned position.

Accordingly, embodiments described herein may comprise one or more features that permit independent movement of components of the system receptacle to facilitate fluidically, thermally, and/or electrically engaging biosensor cartridges. Such independent movement may provide tolerance for mating different elements. For example, embodiments described herein may include the joint assembly 610 to permit the mounting assembly 604 to pivot or shift so that the nozzles 642 and 644 and the thermal element 641 are properly aligned with the biosensor cartridge 600. Furthermore, embodiments described herein may include resilient springs 682 and 684 that permit the nozzles 642 and 644, respectively, to separately move along the vertical axis 694. Similarly, embodiments may also include resilient springs 691 and 693 that permit the thermal element 641 to separately move along the vertical axis 694. In addition, the electrical connector 666 may be moveable along the vertical axis 694 and may also include resilient system contacts 674 the project a distance away from the electrical connector 666. The system contacts 674 and/or the cartridge contacts of the biosensor cartridge 600 may have a sufficient wipe distance to tolerate some misalignment between corresponding contacts. Furthermore, the microdevice 628 and/or the biosensor cartridge 600 may also be independently moveable to permit the system receptacle 212 to move the biosensor cartridge 600 when in the desired slot position.

In alternative embodiments, other mounting mechanisms may be used. For example, the mounting assembly 604 is not required to move in a linear manner to engage the alignment assembly 602. The mounting assembly 604 may be rotated about an axis to engage the alignment assembly 602 in a manner similar to a door being moved from an open to a closed position. In addition, the mounting assembly 604 may be independently moveable such that a user may mount the mounting assembly 604 onto the alignment assembly 602 after the biosensor cartridge 600 has been placed in the predetermined orientation or position.

Furthermore, in alternative embodiments, the thermal element may be configured to approach and engage the biosensor cartridge 600 along the first side surface 668. More specifically, the thermal element and the system contacts may engage a common side of the biosensor cartridge 600.

In addition, the resilient force generated by the resilient springs 682, 684, 691, and 693 may be generated by other mechanisms. For example, a pneumatic system may be operatively coupled to the thermal element 641 and nozzles 642 and 644 used to provide the resilient force.

Although the system receptacle 212 was described above with respect to being part of the workstation 200, the system receptacle 212 may also be configured to operate with other bioassay systems. Furthermore, the system receptacle 212 is not required to be located within a workstation housing, but may be a separate apparatus that is remotely located from the workstation.

Figure 28:
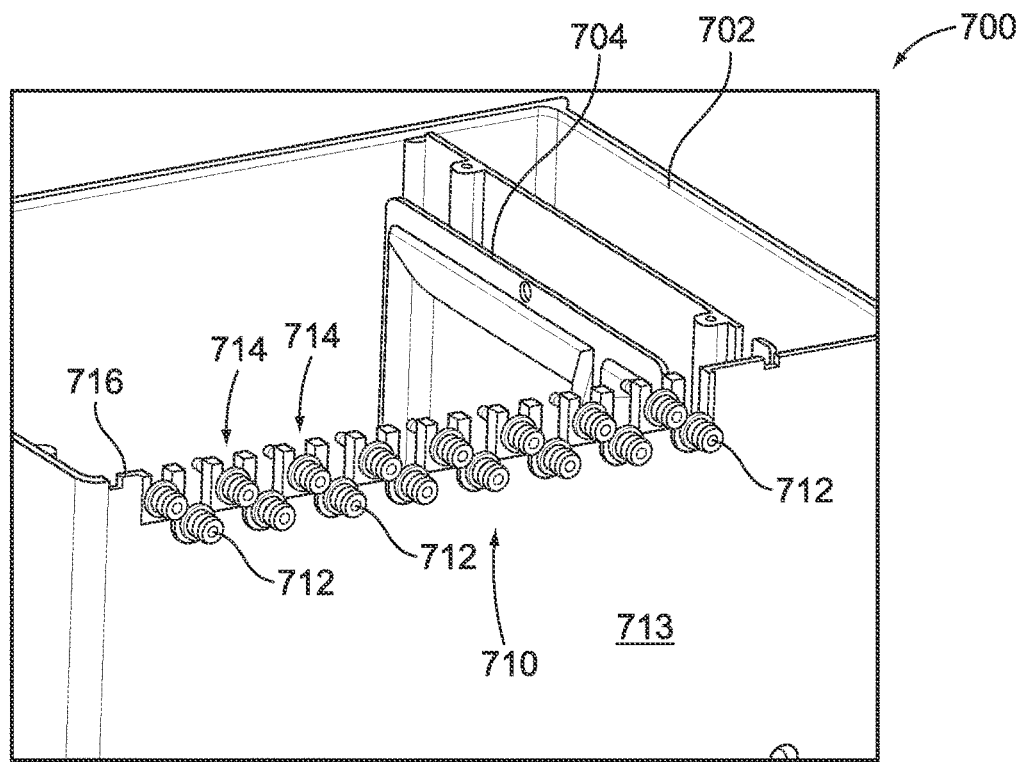
FIG. 28 is a partial perspective view of a fluid storage unit formed m accordance with one embodiment.
Figure 29:
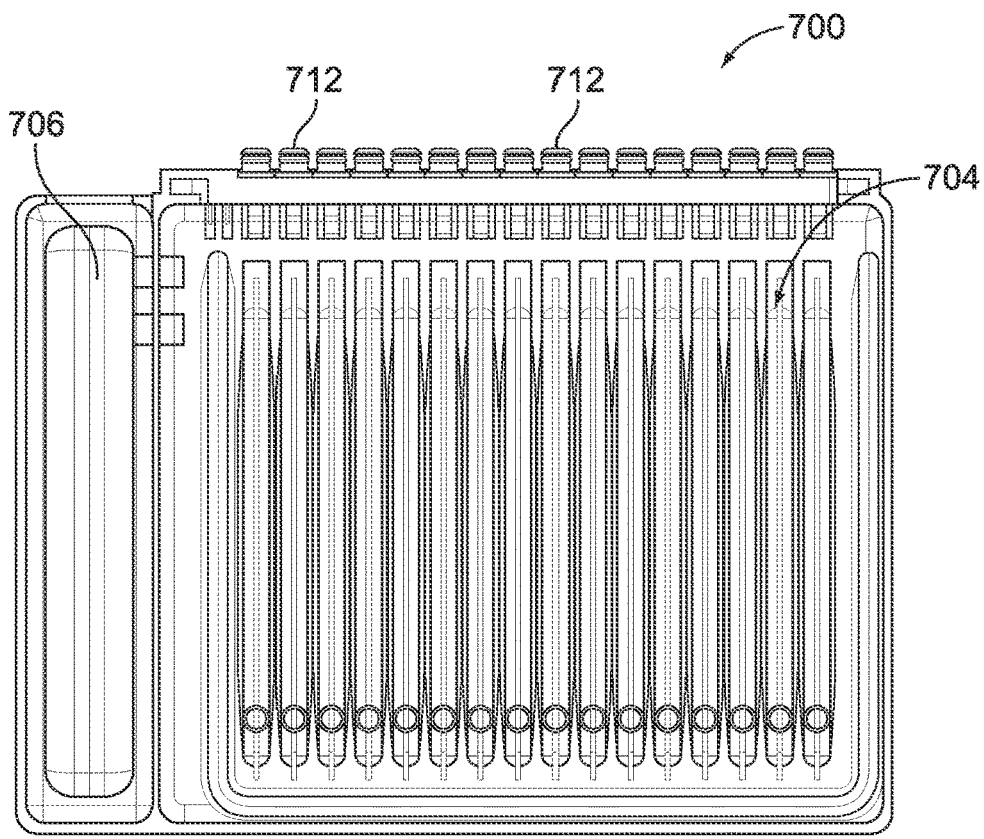
FIG. 29 is a top plan view of the storage unit of FIG. 28.
Figure 30:
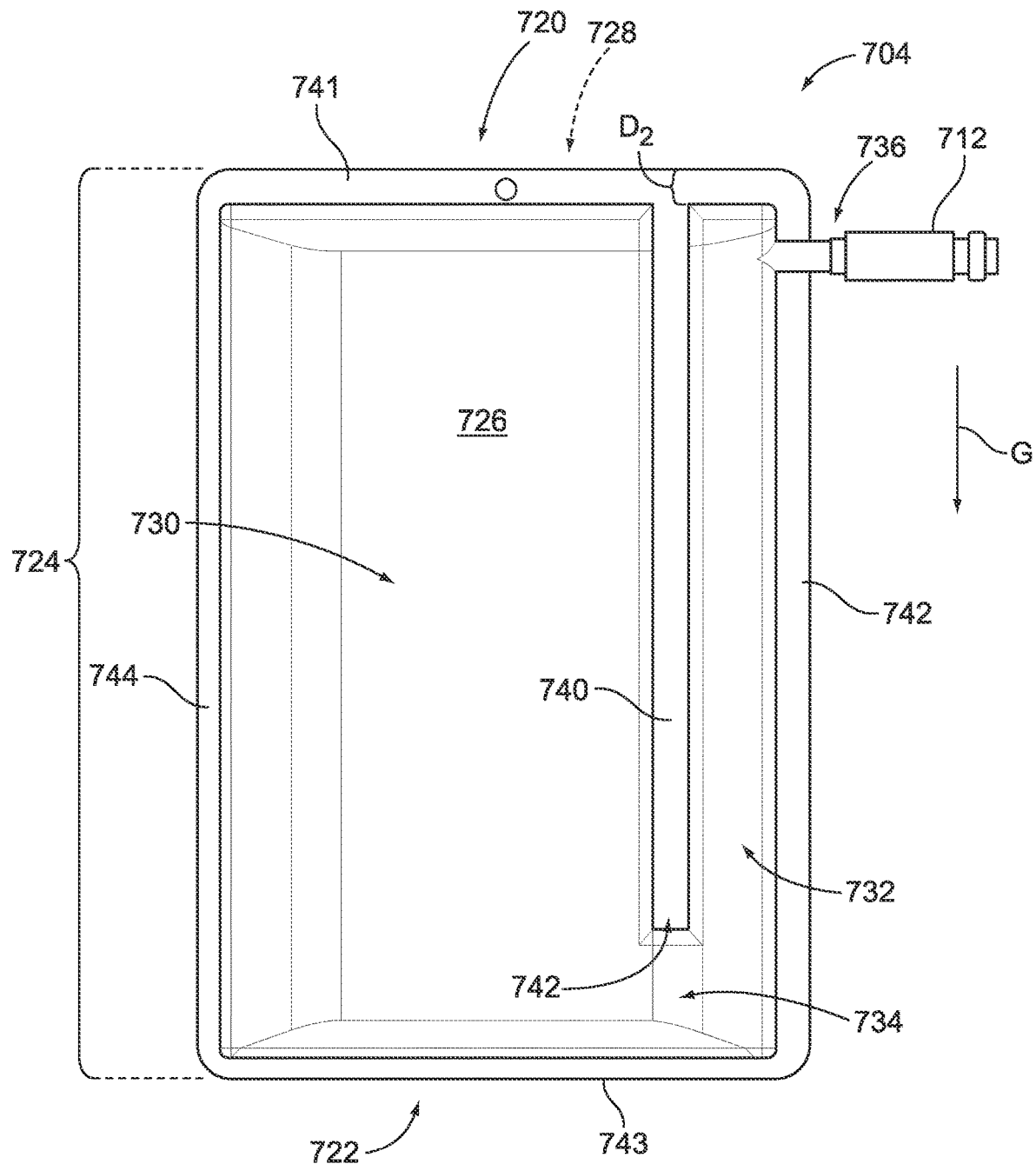
FIG. 30 is a side view of a fluid reservoir bag formed in accordance with one embodiment.

FIGS. 28, 29, and 30 illustrate a fluid storage unit 700 that may be used to store fluids for the workstation 200 (FIG. 3). FIGS. 28 and 29 provide a partial perspective view and a top plan view of the storage unit 700 with a lid (not shown) of the storage unit 700 removed. As shown, the storage unit 700 includes a bag container 702, a plurality of fluid reservoir bags 704, and a waste reservoir bag 706 (FIG. 29). In the illustrated embodiment, a fluidic control system is configured to remove fluid (e.g., reagents, water, buffer solution, cleaning solution, and the like) from the corresponding reservoir bags 704 to a biosensor cartridge. After flowing through the biosensor cartridge, the fluid may be removed and directed into the waste reservoir bag 706. Only one waste reservoir bag 706 is shown in FIG. 29, but additional waste reservoir bags may be used.

As shown in FIG. 28, the storage unit 700 may include a manifold assembly 710 comprising a plurality of tubes 712 arranged along a side 713 of the bag container 702. The tubes 712 are configured to be inserted into the reservoir bags 704 to fluidicly couple the fluids of the reservoir bags 704 to the fluid network. The tubes 712 may be held by an interference fit formed by the tubes 712 and slots 714 of the bag container 702 (e.g., the tubes 712 may be snap-fit into the slots 714). Adjacent slots 714 may extend from a top edge 716 of the bag container 702 at different distances so that the tubes 712 may have a staggered relationship with respect to each other as shown in FIG. 28. Although not shown, when the lid is positioned over a top of the bag container 702, the lid may facilitate holding the tubes 712 in a desired position. The tubes 712 may project from the side 713 of the bag container 702.

FIG. 30 is a side view of the exemplary reservoir bag 704 that is formed in accordance with one embodiment. As shown, the reservoir bag 704 may have a top end 720, a bottom end 722, and a height 724 that extends therebetween. The reservoir bag 704 may be defined by edges 741-644. When in operation, the height 724 may extend in a direction along the gravitational force G. In the illustrated embodiment, the reservoir bag 704 includes a pair of opposite flexible walls 726 and 728 that bonded together. However, in alternative embodiments, the reservoir bag 704 may include only one wall that includes the features described herein. The flexible walls 726 and 728 may define a variable volume for holding a fluid. For example, the flexible walls 726 and 728 may collapse toward each other as fluid is removed from the volume. As shown, the volume includes a main storage portion 730, a flow path portion 732, and a bridge portion 734. The main storage portion 730 and the flow path portion 732 are in fluid communication with each other through the bridge portion 734. Furthermore, the reservoir bag 704 may include a bag opening 736 that is located proximate to the top end 720. The bag opening 736 is configured to fluidically engage a corresponding one of the tubes 712.

As shown in FIG. 30, the reservoir bag 704 includes a partition 740 where the flexible walls 726 and 728 are bonded together that extends from the top end 720 (or top edge 741) and toward the bottom end 722 (or bottom edge 743). The partition 740 may extend to a distal tip 745 that is proximate to the bottom end 722. As shown, the bridge portion 734 is located between the distal tip 745 and the bottom end 722. In the illustrated embodiment, the main storage portion 730 of the volume is greater than the flow path portion 732 of the volume. Furthermore, the bag opening 736 may be located at distance $D_2$ away from the top end 720 or top edge 741. The distance $D_2$ may be configured to permit some air to collect proximate to the top end 720 in the flow path portion 732 without the air being removed through the bag opening 736.

Accordingly, when the fluid is removed from the reservoir bag 704, the fluid flowing from the main storage portion 730 flows to the flow path portion 732 through the bridge portion 734. Fluid from the flow path portion 732 flows through the bag opening 736 to the fluid network. As such, fluid is drawn from proximate to the bottom end 722 to reduce a probability of air being removed with the fluid. As shown, air may collect within the volume proximate to the top end 720 in both the main storage and flow path portions 730 and 732.

In the illustrated embodiment, the flexible walls 726 and 728 are bonded by heat-pressing portions of the flexible walls 726 and 728 together. In particular embodiments, the flexible walls 726 and 728 may be heat-pressed in a single heat-pressing step to form the partition 740, the edges 741-644, and the bag opening 736 of the reservoir bag 704. However, in alternative embodiments, the flexible walls 726 and 728 may be held together by alternative methods, such as an adhesive or a suitable thread.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the specific components and processes described herein are intended to define the parameters of the various embodiments of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

What is claimed is:
1. A system receptacle configured to engage a biosensor cartridge, the system receptacle comprising:
an alignment assembly configured to hold the biosensor cartridge in a predetermined orientation;
an upstream conduit for providing fluid to the biosensor cartridge and a downstream conduit for removing the fluid from the biosensor cartridge, the upstream and downstream conduits including respective nozzles;

an actuation device configured to move the nozzles of the upstream and downstream conduits toward the biosensor cartridge to establish a fluidic connection;

a mounting assembly that includes the nozzles of the upstream and downstream conduits, the mounting assembly configured to be moved by the actuation device to an engaged position with respect to the alignment assembly, wherein the mounting assembly includes a thermal element configured to engage and control a temperature of the biosensor cartridge, the thermal element and the nozzles being held with respect to each other and engaging a common side of the biosensor cartridge.

2. The system receptacle in accordance with claim 1 wherein the actuation device comprises a linear actuator operatively coupled to the conduits, the linear actuator moving the nozzles of the upstream and downstream conduits in an axial direction to and from the biosensor cartridge.

3. The system receptacle in accordance with claim 1 wherein the thermal element and the nozzles are separately moveable in the axial direction to facilitate thermally and fluidicly engaging the biosensor cartridge.

4. The system receptacle in accordance with claim 1 further comprising an electrical connector configured to electrically engage the biosensor cartridge, the electrical connector comprising system contacts configured to electrically engage cartridge contacts of the biosensor cartridge.

5. The system receptacle in accordance with claim 4 wherein the electrical connector is moveable from an unmated position, wherein the system contacts of the electrical connector are spaced apart from cartridge contacts of the biosensor cartridge, to a mated position where the system and cartridge contacts are electrically engaged.

6. The system receptacle in accordance with claim 4 wherein the electrical connector is configured to engage the biosensor cartridge on a first side surface and the nozzles are configured to engage the biosensor cartridge on an opposite second side surface.

7. The system receptacle in accordance with claim 1 wherein the alignment assembly includes guiderails configured to engage the biosensor cartridge, the guiderails directing the biosensor cartridge to the predetermined orientation.

8. The system receptacle in accordance with claim 1 further comprising a joint assembly that operatively couples the mounting assembly to the actuation device, the joint assembly being configured to permit the mounting assembly to at least one of pivot and shift when moved toward an engaged position with the alignment assembly.

* * * * *